(12) United States Patent
Yoon et al.

(10) Patent No.: US 11,412,760 B2
(45) Date of Patent: Aug. 16, 2022

(54) *ESCHERICHIA COLI* BACTERIOPHAGE ESC-COP-7, AND USE THEREOF FOR SUPPRESSING PROLIFERATION OF PATHOGENIC *ESCHERICHIA COLI*

(71) Applicant: INTRON BIOTECHNOLOGY, INC., Gyeonggi-do (KR)

(72) Inventors: Seong Jun Yoon, Seoul (KR); Soo Youn Jun, Seoul (KR); Hyoun Rok Paik, Incheon (KR); Jee Soo Son, Seoul (KR); SAng Hyeon Kang, Seoul (KR)

(73) Assignee: INTRON BIOTECHNOLOGY, INC.

( * ) Notice: Subject to any disclaimer, the term of this patent is extended or adjusted under 35 U.S.C. 154(b) by 600 days.

(21) Appl. No.: 16/464,875

(22) PCT Filed: Sep. 29, 2017

(86) PCT No.: PCT/KR2017/010955
§ 371 (c)(1),
(2) Date: May 29, 2019

(87) PCT Pub. No.: WO2018/101594
PCT Pub. Date: Jun. 7, 2018

(65) Prior Publication Data
US 2019/0321424 A1  Oct. 24, 2019

(30) Foreign Application Priority Data
Nov. 30, 2016 (KR) .................... 10-2016-0161320

(51) Int. Cl.
*A61K 35/76* (2015.01)
*A23K 10/16* (2016.01)
*A23K 30/18* (2016.01)
*C12N 7/00* (2006.01)
*A01N 63/40* (2020.01)

(52) U.S. Cl.
CPC .............. *A23K 10/16* (2016.05); *A01N 63/40* (2020.01); *A23K 30/18* (2016.05); *A61K 35/76* (2013.01); *C12N 7/00* (2013.01); *C12N 2795/10111* (2013.01); *C12N 2795/10131* (2013.01); *C12N 2795/10132* (2013.01)

(58) Field of Classification Search
CPC ........ A23K 10/16; A23K 30/18; A23K 10/18; A01N 63/40; A01N 63/00; A61K 35/76; C12N 7/00; C12N 2795/10132; C12N 2795/10131; C12N 2795/10111
See application file for complete search history.

(56) References Cited

U.S. PATENT DOCUMENTS

| | | | |
|---|---|---|---|
| 9,433,653 B2 | 9/2016 | Yoon et al. | |
| 10,265,353 B2 | 4/2019 | Yoon et al. | |
| 10,265,354 B2 | 4/2019 | Yoon et al. | |
| 10,265,356 B2 | 4/2019 | Yoon et al. | |

FOREIGN PATENT DOCUMENTS

| | | |
|---|---|---|
| KR | 10-2015-0127321 A | 11/2015 |
| KR | 10-2016-0080176 A | 7/2016 |
| KR | 10-2016-0080575 A | 7/2016 |
| KR | 10-2016-0080577 A | 7/2016 |

OTHER PUBLICATIONS

Jamalludeen, N. et al., Complete Genomic Sequence of Bacteriophage ϕEcoM-GJ1, a Novel Phage That Has Myovirus Morphology and a Podovirus-Like RNA Polymerase. Appl Environ Microbiol. 2008; 74(2):516-25.

International Search Report and Written Opinion dated Jan. 19, 2018 by the International Searching Authority for Patent Application No. PCT/KR2017/010955, which was filed on Sep. 29, 2017 and published as WO 2018/101594 on Jun. 7, 2018 (Inventor—Yoon et al.; Applicant—Intron Biotechnology Co., Ltd.) (Original-9 pages; Translation—5 pages).

*Primary Examiner* — Allison M Fox
*Assistant Examiner* — Qing Xu
(74) *Attorney, Agent, or Firm* — Ballard Spahr LLP

(57) ABSTRACT

The present invention relates to a *Myoviridae* bacteriophage ESC-COP-7 (accession number KCTC 13130BP) isolated from nature, and a method for preventing and treating infections from pathogenic *Escherichia coli* by means of a composition containing the Myoviridae bacteriophage ESC-COP-7 as an active ingredient, the *Myoviridae* bacteriophage ESC-COP-7 being characterized by having the capability to specifically kill *Escherichia coli*, and genome expressed by the SEQ ID 1.

2 Claims, 1 Drawing Sheet
Specification includes a Sequence Listing.

[FIG. 1]
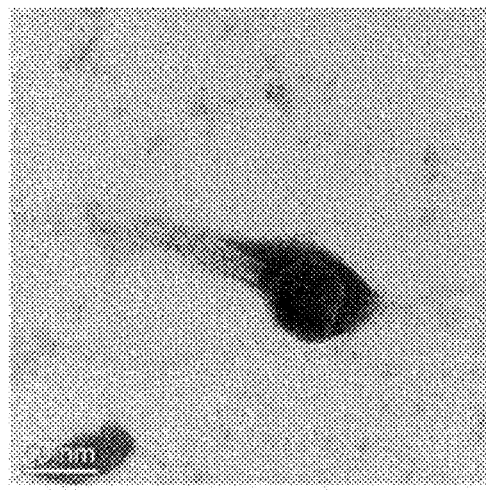
[FIG. 2]
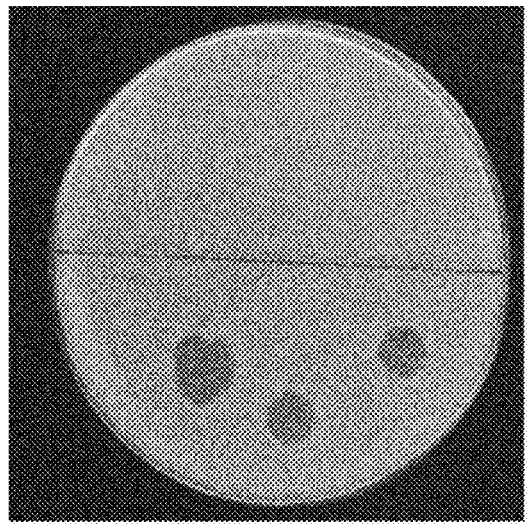

ESCHERICHIA COLI BACTERIOPHAGE ESC-COP-7, AND USE THEREOF FOR SUPPRESSING PROLIFERATION OF PATHOGENIC ESCHERICHIA COLI

CROSS-REFERENCE TO RELATED APPLICATIONS

This application is a U.S. National Phase Application of International Application No. PCT/KR2017/010955, filed Sep. 29, 2017, which claims priority to Korean Application No. 10-2016-0161320, filed Nov. 30, 2016, each of which are hereby incorporated by reference in their entirety.

REFERENCE TO SEQUENCE LISTING

The Sequence Listing submitted Dec. 13, 2018 as a text file named "08162_0053U1_Sequence_Listing.txt," created on May 29, 2019, and having a size of 69,171 bytes is hereby incorporated by reference pursuant to 37 C.F.R. § 1.52(e)(5).

TECHNICAL FIELD

The present invention relates to a bacteriophage isolated from nature, which infects *Escherichia coli* to thus kill *Escherichia coli,* and a method for preventing and treating a pathogenic Escherichia coli infection using a composition including the same as an active ingredient. More particularly, the present invention relates to a *Myoviridae* bacteriophage Esc-COP-7 (Accession number: KCTC 13130BP) isolated from nature, which has the ability to specifically kill *Escherichia coli* and which includes a genome expressed by SEQ. ID. NO: 1, and a method for preventing a pathogenic *Escherichia coli* infection and a treatment method after the pathogenic *Escherichia coli* infection using a composition including the bacteriophage as an active ingredient.

BACKGROUND ART

*Escherichia coli* belongs to the intestinal microflora, is a gram-negative bacillus and a catalase-positive, oxidase-negative, and facultative anaerobic bacterium, and most examples thereof degrade lactose. *Escherichia coli* is serologically subdivided according to whether it contains a somatic (O), flagellar (H) or capsular (K) antigen, and these antigens are known to be associated with the pathogenicity of *Escherichia coli*. Pathogenic *Escherichia coli* refers to *Escherichia coli* that has acquired a small number of the virulence factors capable of being expressed in *Escherichia coli*, and, depending on the onset characteristics and the kind of toxin, there are five types of *Escherichia coli,* namely enterohemorrhagic *Escherichia coli,* enterotoxigenic *Escherichia coli,* enteroinvasive *Escherichia coli,* enteropathogenic *Escherichia coli,* and enteroaggregative *Escherichia coli.* Pathogenic *Escherichia coli* in livestock infects various ages thereof to thus cause disease, and the main symptom thereof is diarrhea, and mortality due to extreme dehydration is very high. Diarrhea caused by pathogenic *Escherichia coli* is known to be the main disease that afflicts almost all livestock farming in Korea, and the damage to the livestock industry is regarded as significant.

Generally, vaccines and antibiotics are used for the prevention and treatment of infectious diseases of pathogenic *Escherichia coli*. Here, the effectiveness of antibiotics has been continuously decreasing due to the increase of antibiotic-resistant bacteria, and the development of effective methods other than antibiotics is required due to the increased number of regulations on the use of antibiotics in animals.

Recently, the use of bacteriophages as a countermeasure against bacterial diseases has attracted considerable attention. In particular, interest in bacteriophages is higher than ever due to the preference for environmentally friendly methods. Bacteriophages are very small microorganisms infecting bacteria, and are usually simply called "phages". Once a bacteriophage infects bacteria, the bacteriophage is proliferated inside the bacterial cell. After proliferation, the progeny of the bacteriophage destroy the bacterial cell wall and escapes from the host bacteria, suggesting that the bacteriophage has the ability to kill bacteria. The manner in which the bacteriophage infects bacteria is characterized by the very high specificity thereof, and thus the number of types of bacteriophages infecting a specific bacterium is limited. That is, a certain bacteriophage can infect only a specific bacterium, suggesting that a certain bacteriophage can kill only a specific bacterium and cannot harm other bacteria. Due to this bacteria specificity of bacteriophages, the bacteriophage confers antibacterial effects only upon target bacteria, but does not affect commensal bacteria in the environment or in animals. Conventional antibiotics, which have been widely used for bacterial treatment, incidentally influence many kinds of bacteria. This causes problems such as environmental pollution and the disturbance of normal flora in animals. On the other hand, the use of bacteriophages does not disturb normal flora in animals, because the target bacterium is selectively killed. Hence, the bacteriophage may be utilized safely, which thus greatly lessens the probability of adverse actions in use compared to any other antibiotics.

Bacteriophages were first discovered by the English bacteriologist Twort in 1915 when he noticed that Micrococcus colonies melted and became transparent by something unknown. In 1917, the French bacteriologist d'Herelle discovered that Shigella dysenteriae in the filtrate of dysentery patient feces was melted by something, and further studied this phenomenon. As a result, he independently identified bacteriophages, and named them bacteriophages, which means "eater of bacteria". Since then, various bacteriophages acting against such pathogenic bacteria as Shigella, Salmonella Typhi, and Vibrio cholerae have been continuously identified.

Owing to the unique ability of bacteriophages to kill bacteria, bacteriophages have attracted anticipation as a potentially effective countermeasure against bacterial infection since their discovery, and there has been a lot of research related thereto. However, since penicillin was discovered by Fleming, studies on bacteriophages have continued only in some Eastern European countries and the former Soviet Union, because the spread of antibiotics was generalized. Since 2000, the limitations of conventional antibiotics have appeared due to the increase in antibiotic-resistant bacteria, and the possibility of developing bacteriophages as a substitute for conventional antibiotics has been highlighted, so that bacteriophages are again attracting attention as antibacterial agents. In particular, recently, government regulations for the use of antibiotics have become more stringent around the world, and thus interest in bacteriophages is increasing and the range of industrial applications therefore is continually broadening.

As demonstrated above, bacteriophages tend to be highly specific for bacteria. Because of this specificity, bacteriophages frequently exhibit an antibacterial effect only for certain strains of bacteria, even though the bacteria belong to the same species. In addition, the antibacterial strength of bacteriophages may depend on the type of target bacterial strain.

Therefore, it is necessary to collect many kinds of bacteriophages that are useful in order to get effective control of specific bacteria. Hence, in order to develop the effective bacteriophage utilization method in response to pathogenic *Escherichia coli,* many kinds of bacteriophages that exhibit antibacterial action against *Escherichia coli* must be acquired. Furthermore, the resulting bacteriophages need to be screened as to whether or not they are superior to others from the aspect of antibacterial strength and spectrum.

DISCLOSURE

Technical Problem

Therefore, the present inventors endeavored to develop a composition applicable for the prevention or treatment of a pathogenic *Escherichia coli* infection using a bacteriophage that is isolated from nature and is capable of selectively killing *Escherichia coli,* and further to establish a method for preventing or treating a pathogenic *Escherichia coli* infection using the composition. As a result, the present inventors isolated a bacteriophage suitable for this purpose from nature and secured the gene sequence of the genome that distinguishes the isolated bacteriophage from other bacteriophages. Then, the present inventors developed a composition including the bacteriophage as an active ingredient, and identified that this composition is capable of being used to effectively prevent and treat a pathogenic *Escherichia coli* infection, leading to the completion of the present invention.

Accordingly, it is an object of the present invention to provide a Myoviridae bacteriophage Esc-COP-7 (Accession number: KCTC 13130BP) isolated from nature, which has the ability to specifically kill *Escherichia coli* and which includes the genome expressed by SEQ. ID. NO: 1.

It is another object of the present invention to provide a composition applicable for preventing a pathogenic *Escherichia coli* infection, which includes a bacteriophage Esc-COP-7 infecting *Escherichia coli* to thus kill *Escherichia coli* as an active ingredient, and a method for preventing a pathogenic *Escherichia coli* infection using said composition.

It is another object of the present invention to provide a composition applicable for treating a pathogenic *Escherichia coli* infection, which includes a bacteriophage Esc-COP-7 infecting *Escherichia coli* to thus kill *Escherichia coli* as an active ingredient, and a method for treating a pathogenic *Escherichia coli* infection using said composition.

It is another object of the present invention to provide a disinfectant for preventing and treating a pathogenic *Escherichia coli* infection using said composition.

It is another object of the present invention to provide a drinking-water additive for preventing and treating a pathogenic *Escherichia coli* infection using said composition.

It is another object of the present invention to provide a feed additive effective upon farming by preventing and treating a pathogenic *Escherichia coli* infection using said composition.

Technical Solution

The present invention provides a Myoviridae bacteriophage Esc-COP-7 (Accession number: KCTC 13130BP) isolated from nature, which has the ability to specifically kill *Escherichia coli* and which includes a genome expressed by SEQ. ID. NO: 1, and a method for preventing and treating a pathogenic *Escherichia coli* infection using a composition including the same as an active ingredient.

The bacteriophage Esc-COP-7 was isolated by the present inventors and then deposited at Korea Collection for Type Cultures, Korea Research Institute of Bioscience and Biotechnology on Oct. 17, 2016 (Accession number: KCTC 13130BP).

The present invention also provides a disinfectant, a drinking-water additive, and a feed additive applicable for the prevention or treatment of a pathogenic *Escherichia coli* infection, which include the bacteriophage Esc-COP-7 as an active ingredient.

Since the bacteriophage Esc-COP-7 included in the composition of the present invention kills *Escherichia coli* effectively, it is considered effective in the prevention (prevention of infection) or treatment (treatment of infection) of diseases caused by pathogenic *Escherichia coli.* Therefore, the composition of the present invention is capable of being utilized for the prevention and treatment of diseases caused by pathogenic *Escherichia coli.*

In this description, the terms "prevention" and "prevent" indicate (i) to block a pathogenic *Escherichia coli* infection; and (ii) to inhibit the progression of diseases caused by a pathogenic *Escherichia coli* infection.

In this description, the terms "treatment" and "treat" indicate all actions that (i) suppress diseases caused by pathogenic *Escherichia coli;* and (ii) alleviate the pathological condition of the diseases caused by pathogenic *Escherichia coli.*

In this description, the terms "isolate", "isolating", and "isolated" indicate actions which isolate bacteriophages from nature by applying diverse experimental techniques and which secure characteristics that can distinguish the target bacteriophage from others, and further include the action of proliferating the target bacteriophage using bioengineering techniques so that the target bacteriophage is industrially applicable.

The pharmaceutically acceptable carrier included in the composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may additionally include lubricants, wetting agents, sweeteners, flavors, emulsifiers, suspending agents, and preservatives, in addition to the above ingredients.

In the composition of the present invention, the bacteriophage Esc-COP-7 is included as an active ingredient. The bacteriophage Esc-COP-7 is included at a concentration of $1 \times 10^1$ pfu/ml to $1 \times 10^{30}$ pfu/ml or $1 \times 10^1$ pfu/g to $1 \times 10^{30}$ pfu/g, and preferably at a concentration of $1 \times 10^4$ pfu/ml to $1 \times 10^{15}$ pfu/ml or $1 \times 10^4$ pfu/g to $1 \times 10^{15}$ pfu/g.

The composition of the present invention can be formulated according to a method that can be easily performed by those of ordinary skill in the art to which the present invention pertains using a pharmaceutically acceptable carrier and/or excipient in the form of a unit dose or in a multi-dose container. Then, the formulation may be in the form of a solution, suspension, or emulsion in oil or a water-soluble medium, extract, powder, granule, tablet, or capsule. A dispersing agent or stabilizer may be additionally included.

The composition of the present invention may be prepared as a disinfectant, a drinking-water additive, and a feed additive according to the purpose of use, without limitation thereto.

In order to improve the effectiveness of above purpose, bacteriophages that confer antibacterial activity against other bacterial species may be further included in the composition of the present invention. In addition, other kinds of bacteriophages that have antibacterial activity against *Escherichia coli* may be further included in the composition of the present invention. These bacteriophages may be combined properly so as to maximize antibacterial effects, because their antibacterial activities against *Escherichia coli* may be different from the aspects of antibacterial strength and spectrum.

Advantageous Effects

The method for preventing and treating a pathogenic *Escherichia coli* infection using the composition including the bacteriophage Esc-COP-7 as an active ingredient according to the present invention may have the advantage of very high specificity for *Escherichia coli*, compared with conventional methods based on chemical materials including existing antibiotics. This means that the composition can be used for preventing or treating a pathogenic *Escherichia coli* infection without affecting other bacteria, namely useful commensal bacteria, and has fewer side effects attributable to the use thereof. In general, when chemical materials such as antibiotics are used, commensal bacteria are also damaged, thus weakening immunity in animals and entailing various side effects owing to the use thereof. Further, the composition of the present invention uses a bacteriophage isolated from nature as an active ingredient, and thus it is very environmentally friendly. Meanwhile, in the case of bacteriophages exhibiting antibacterial activity against the same species of bacteria, each antibacterial activity of the bacteriophages are different with regard to antibacterial strength and spectrum [the spectrum of the antibacterial activity of the bacteriophages applied to individual bacteria strains in terms of the strains of various bacteria belonging to *Escherichia coli*. Typically, bacteriophages are usually effective only on some bacterial strains, even within the same species. That is to say, the antibacterial activity of bacteriophages may depend on the bacterial strain even for the same species of bacteria]. Accordingly, the present invention may provide antibacterial activity against *Escherichia coli* different to that provided by other bacteriophages acting on *Escherichia coli*. This provides significantly different applicability to industrial fields.

DESCRIPTION OF DRAWINGS

FIG. 1 is an electron micrograph showing the morphology of the bacteriophage Esc-COP-7.

FIG. 2 is a photograph showing the results of an experiment on the ability of the bacteriophage Esc-COP-7 to kill *Escherichia coli*. The clear zone is a plaque formed by lysis of the target bacteria.

MODE FOR INVENTION

Hereinafter, the present invention will be described in more detail with reference to Examples. However, the Examples are merely examples of the present invention, and the scope of the present invention is not limited to the Examples.

Example 1: Isolation of Bacteriophage Capable of Killing *Escherichia coli*

Samples were collected from nature to isolate the bacteriophage capable of killing *Escherichia coli*. Here, the *Escherichia coli* strains used for the bacteriophage isolation had been previously isolated and identified as pathogenic *Escherichia coli* by the present inventors.

The procedure for isolating the bacteriophage is described in detail hereinafter. The collected sample was added to a TSB (Tryptic Soy Broth) culture medium (casein digest, 17 g/L; soybean digest, 3 g/L; dextrose, 2.5 g/L; NaCl, 5 g/L; dipotassium phosphate, 2.5 g/L) inoculated with *Escherichia coli* at a ratio of 1/1000, followed by shaking culture at 37° C. for 3 to 4 hours. Upon completion of the culture, centrifugation was performed at 8,000 rpm for 20 minutes and a supernatant was recovered. The recovered supernatant was inoculated with *Escherichia coli* at a ratio of 1/1000, followed by shaking culture at 37° C. for 3 to 4 hours. When the sample contained the bacteriophage, the above procedure was repeated a total of 5 times in order to sufficiently increase the number (titer) of the bacteriophage. After repeating the procedure 5 times, the culture solution was subjected to centrifugation at 8,000 rpm for 20 minutes. After the centrifugation, the recovered supernatant was filtered using a 0.45 μm filter. The obtained filtrate was used in a typical spot assay for examining whether or not a bacteriophage capable of killing *Escherichia coli* was included therein.

The spot assay was performed as follows: TSB culture medium was inoculated with *Escherichia coli* at a ratio of 1/1000, followed by shaking culture at 37° C. overnight. 3 ml ($OD_{600}$ of 1.5) of the culture solution of *Escherichia coli* prepared above was spread on TSA (casein digest, 15 g/L; soybean digest, 5 g/L; NaCl, 5 g/L; agar, 15 g/L) plate. The plate was left on a clean bench for about 30 minutes to dry the spread solution. After drying, 10 μl of the prepared filtrate was spotted onto the plate culture medium on which *Escherichia coli* was spread and then left to dry for about 30 minutes. After drying, the plate culture medium that was subjected to spotting was stationary-cultured at 37° C. for one day, and then examined for the formation of clear zones at the positions where the filtrate was dropped. In the case of the filtrate generated a clear zone, it is judged that the bacteriophage capable of killing *Escherichia coli* is included therein. Through the above examination, the filtrate containing the bacteriophage having the ability to kill *Escherichia coli* could be obtained.

The pure bacteriophage was isolated from the filtrate confirmed above to have the bacteriophage capable of killing *Escherichia coli*. A conventional plaque assay was used to isolate the pure bacteriophage. In detail, a plaque formed in the course of the plaque assay was recovered using a sterilized tip, which was then added to the culture solution of *Escherichia coli*, followed by culturing at 37° C. for 4 to 5 hours. After the culturing, centrifugation was performed at 8,000 rpm for 20 minutes to obtain a supernatant. The *Escherichia coli* culture solution was added to the obtained supernatant at a volume ratio of 1/50, followed by culturing at 37° C. for 4 to 5 hours. In order to increase the number of bacteriophages, the above procedure was repeated at least 5 times. Then, centrifugation was performed at 8,000 rpm for 20 minutes in order to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, a solution containing the pure bacteriophage was obtained. The procedure for isolating the pure bacteriophage was generally repeated until the generated plaques became similar to each other in size and morphology. In addition, final isolation of the pure bacteriophage was confirmed using electron microscopy. The above procedure was repeated until the isolation of the pure bacteriophage was confirmed using electron microscopy. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics, the novel bacteriophage isolated above was confirmed to belong to the *Myoviridae* bacteriophage.

The solution containing the pure bacteriophage confirmed above was subjected to the following purification process. The *Escherichia coli* culture solution was added to the solution containing the pure bacteriophage at a volume ratio of 1/50 based on the total volume of the bacteriophage solution, followed by further culturing for 4 to 5 hours.

After the culturing, centrifugation was performed at 8,000 rpm for 20 minutes to obtain a supernatant. This procedure was repeated a total of 5 times in order to obtain a solution containing sufficient numbers of the bacteriophage. The supernatant obtained from the final centrifugation was filtered using a 0.45 µm filter, followed by a conventional polyethylene glycol (PEG) precipitation process. Specifically, PEG and NaCl were added to 100 ml of the filtrate until reaching 10% PEG 8000/0.5 M NaCl, and then left at 4° C. for 2 to 3 hours. Thereafter, centrifugation was performed at 8,000 rpm for 30 minutes to obtain the bacteriophage precipitate. The resulting bacteriophage precipitate was suspended in 5 ml of a buffer (10 mM Tris-HCl, 10 mM MgSO$_4$, 0.1% gelatin, pH 8.0). The resulting material was referred to as a bacteriophage suspension or bacteriophage solution.

As a result, the pure bacteriophage purified above was collected, was named the bacteriophage Esc-COP-7, and then deposited under the Budapest Treaty on the International Procedure at Korea Collection for Type Cultures, Korea Research Institute of Bioscience and Biotechnology (KRIBB), 125 Gwahak-ro, Yuseong-gu, Daijeon 305-806, Republic of Korea; the deposit was made on Oct. 17, 2016 (Accession number: KCTC 13130BP).

Example 2: Separation and Sequence Analysis of Genome of Bacteriophage Esc-COP-7

The genome of the bacteriophage Esc-COP-7 was separated as follows. The genome was separated from the bacteriophage suspension obtained using the same method as in Example 1. First, in order to eliminate DNA and RNA of *Escherichia coli* included in the suspension, 200 U of each of DNase I and RNase A was added to 10 ml of the bacteriophage suspension and then left at 37° C. for 30 minutes. After being left for 30 minutes, in order to remove the DNase I and RNase A activity, 500 µl of 0.5 M ethylenediaminetetraacetic acid (EDTA) was added thereto and then left for 10 minutes. In addition, the resulting mixture was further left at 65° C. for 10 minutes, and 100 µl of proteinase K (20 mg/ml) was then added thereto so as to break the outer wall of the bacteriophage, followed by reaction at 37° C. for 20 minutes. After that, 500 µl of 10% sodium dodecyl sulfate (SDS) was added thereto, followed by reaction at 65° C. for 1 hour. After reaction for 1 hour, 10 ml of the solution of phenol:chloroform:isoamyl alcohol, mixed at a component ratio of 25:24:1, was added to the reaction solution, followed by mixing thoroughly. In addition, the resulting mixture was subjected to centrifugation at 13,000 rpm for 15 minutes to separate layers. Among the separated layers, the upper layer was selected, and isopropyl alcohol was added thereto at a volume ratio of 1.5, followed by centrifugation at 13,000 rpm for 10 minutes in order to precipitate the genome. After collecting the precipitate, 70% ethanol was added to the precipitate, followed by centrifugation at 13,000 rpm for 10 minutes to wash the precipitate. The washed precipitate was recovered, vacuum-dried and then dissolved in 100 µl of water. This procedure was repeated to obtain a sufficient amount of the genome of the bacteriophage Esc-COP-7.

Information on the sequence of the genome of the bacteriophage Esc-COP-7 obtained above was secured by performing next-generation sequencing analysis using Illumina Mi-Seq equipment from the National Instrumentation Center for Environmental Management, Seoul National University. The finally analyzed genome of the bacteriophage Esc-COP-7 had a size of 54,200 bp, and the sequence of whole genome was expressed by SEQ. ID. NO: 1.

The homology (similarity) of the bacteriophage Esc-COP-7 genomic sequence obtained above with previously reported bacteriophage genomic sequences was investigated using BLAST (www.ncbi.nlm.nih.gov/BLAST/) on the web. As a result of the BLAST investigation, the genomic sequence of the bacteriophage Esc-COP-7 was found to have a relatively high homology with the sequence of the *Escherichia coli* bacteriophage phiEcoM-GJ1 (Genbank Accession No. EF460875.1) (identity: 89%). However, the number of open reading frames (ORFs) on the bacteriophage Esc-COP-7 genome is 77, whereas *Escherichia coli* bacteriophage phiEcoM-GJ1 has 75 open reading frames, unlike the bacteriophage Esc-COP-7.

Based upon this result, it is concluded that the bacteriophage Esc-COP-7 must be a novel bacteriophage different from conventionally reported bacteriophages. Further, since the antibacterial strength and spectrum of bacteriophages typically depend on the type of bacteriophage, it is considered that the bacteriophage Esc-COP-7 can provide antibacterial activity different from that of any other bacteriophages reported previously.

Example 3: Investigation of Ability of Bacteriophage Esc-COP-7 to Kill Pathogenic *Escherichia coli*

The ability of the isolated bacteriophage Esc-COP-7 to kill pathogenic *Escherichia coli* was investigated. In order to investigate the killing ability, the formation of clear zones was observed using the spot assay in the same manner as described in Example 1. A total of 10 strains that had been isolated and identified as pathogenic *Escherichia coli* by the present inventors were used as pathogenic *Escherichia coli* for the investigation of killing ability. The bacteriophage Esc-COP-7 had the ability to kill a total of 9 strains among 10 strains of pathogenic *Escherichia coli* as the experimental target. The experimental result thereof is shown in FIG. 2. Meanwhile, the ability of the bacteriophage Esc-COP-7 to kill *Bordetella bronchiseptica, Enterococcus faecalis, Enterococcus faecium, Streptococcus mitis, Streptococcus uberis* and *Pseudomonas aeruginosa* was also investigated in a separate experiment. As a result, the bacteriophage Esc-COP-7 did not have the ability to kill these microorganisms.

Therefore, it is confirmed that the bacteriophage Esc-COP-7 has strong ability to kill pathogenic *Escherichia coli* and a broad antibacterial spectrum against pathogenic *Escherichia coli*, suggesting that the bacteriophage Esc-COP-7 can be used as an active ingredient of the composition for preventing and treating pathogenic *Escherichia coli* infection.

Example 4: Experimental Example Regarding Prevention of Pathogenic *Escherichia coli* Infection Using Bacteriophage Esc-COP-7

100 μl of a bacteriophage Esc-COP-7 solution at a level of $1 \times 10^8$ pfu/ml was added to a tube containing 9 ml of a TSB culture medium. To another tube containing 9 ml of a TSB culture medium, only the same amount of TSB culture medium was further added. A pathogenic *Escherichia coli* culture solution was then added to each tube so that absorbance reached about 0.5 at 600 nm. After pathogenic *Escherichia coli* was added, the tubes were transferred to an incubator at 37° C., followed by shaking culture, during which the growth of pathogenic *Escherichia coli* was observed. As presented in Table 1, it was observed that the growth of pathogenic *Escherichia coli* was inhibited in the tube to which the bacteriophage Esc-COP-7 solution was added, while the growth of pathogenic *Escherichia coli* was not inhibited in the tube to which the bacteriophage solution was not added.

TABLE 1

Growth inhibition of pathogenic *Escherichia coli*

| | $OD_{600}$ absorbance value | | |
|---|---|---|---|
| Classification | 0 minutes after culture | 30 minutes after culture | 60 minutes after culture |
| Bacteriophage solution is not added | 0.5 | 0.8 | 1.7 |
| Bacteriophage solution is added | 0.5 | 0.2 | 0.1 |

The above results indicate that the bacteriophage Esc-COP-7 of the present invention not only inhibits the growth of pathogenic *Escherichia coli* but also has the ability to kill pathogenic *Escherichia coli*. Therefore, it is concluded that the bacteriophage Esc-COP-7 can be used as an active ingredient of the composition for preventing a pathogenic *Escherichia coli* infection.

Example 5: Example of Treatment of Infectious Diseases of Pathogenic *Escherichia coli* Using Bacteriophage Esc-COP-7

The therapeutic effect of the bacteriophage Esc-COP-7 on pigs afflicted with pathogenic *Escherichia coli* was investigated. A total of 2 groups of four 25-day-old weaning pigs per group were prepared and reared separately in experimental farming pig pens (1.1 m×1.0 m), and the experiment was performed for 14 days. The environment surrounding the pens under the warming facility was controlled, and the temperature and humidity in the pig pens were maintained constant, and the floor of the pig pen was cleaned every day. On the $7^{th}$ day after the start of the experiment, all pigs were orally administered with a pathogenic *Escherichia coli* solution using an oral injection tube. The administered pathogenic *Escherichia coli* solution was prepared as follows. Pathogenic *Escherichia coli* was cultured at 37° C. for 18 hours using a TSB culture medium, after which the bacteria were isolated and adjusted to $10^9$ CFU/ml using physiological saline (pH 7.2). From the day following administration of the pathogenic *Escherichia coli*, the bacteriophage Esc-COP-7 of $10^9$ PFU was orally administered to the pigs in the experimental group (bacteriophage solution-administered group) twice a day in the same manner as the administration of the pathogenic *Escherichia coli* solution. The pigs in the control group (the group not administered with bacteriophage solution) were not subjected to any treatment. Feed and drinking water were provided to both the control and experimental groups. Diarrhea was examined in all test animals on a daily basis after administration of the pathogenic *Escherichia coli*. The extent of diarrhea was determined by measuring according to a diarrhea index. The diarrhea index was measured using a commonly used Fecal Consistency (FC) score (normal: 0, soft stool: 1, loose diarrhea: 2, severe diarrhea: 3). The results are shown in Table 2.

TABLE 2

Result of measurement of diarrhea index

| Days after administration with pathogenic *E. coli* | 0 | 1 | 2 | 3 | 4 | 5 | 6 |
|---|---|---|---|---|---|---|---|
| Control group (bacteriophage solution not administered) | 1.0 | 1.5 | 1.5 | 1.25 | 1.0 | 1.0 | 0.75 |
| Experimental group (administered with bacteriophage solution) | 0.5 | 0.5 | 0.25 | 0.25 | 0 | 0 | 0 |

From the above results, it is confirmed that the bacteriophage Esc-COP-7 of the present invention could be potentially very effective in the treatment of infectious diseases caused by pathogenic *Escherichia coli*.

Example 6: Preparation of Feed Additives and Feed

Feed additives were prepared using a bacteriophage Esc-COP-7 solution so that a bacteriophage Esc-COP-7 was contained in an amount of $1 \times 10^9$ pfu for 1 g of the feed additives. The method of preparing the feed additives was as follows: Maltodextrin (50%, w/v) was added to the bacteriophage solution, and the resulting mixture was then freeze-dried. Finally, the dried mixture was ground into fine powder. In the above-described preparation procedure, the drying procedure can be replaced with drying under reduced pressure, drying with heat, or drying at room temperature. In order to prepare the control for comparison, the feed additives that did not contain the bacteriophage but contained a buffer (10 mM Tris-HCl, 10 mM $MgSO_4$, 0.1% gelatin, pH 8.0) used to prepare the bacteriophage solution was prepared.

The two kinds of feed additives thus prepared were each mixed with a pig-based feed at a weight ratio of 1,000, thus ultimately preparing two kinds of feed.

Example 7: Preparation of Drinking-Water Additives and Disinfectants

Drinking-water additives and disinfectants were prepared in the same manner because they differ only in utilization and are the same in dosage form. The drinking-water additives (or disinfectants) were prepared using a bacteriophage Esc-COP-7 solution so that a bacteriophage Esc-COP-7 was contained in an amount of $1\times10^9$ pfu for 1 ml of the drinking-water additives (or disinfectants). In the method of preparing the drinking-water additives (or disinfectants), the bacteriophage Esc-COP-7 solution was added so that the bacteriophage Esc-COP-7 was contained in an amount of $1\times10^9$ pfu for 1 ml of the buffer used to prepare the bacteriophage solution, and mixing was sufficiently performed. In order to prepare the control for comparison, the buffer used to prepare the bacteriophage solution itself was used as the drinking-water additive (or disinfectant) that did not contain the bacteriophage.

The prepared two kinds of drinking-water additives (or disinfectants) were diluted with water at a volume ratio of 1,000, thus ultimately preparing drinking-water additives (or disinfectants).

Example 8: Confirmation of Feeding Effect on Pig Farming

Improvement in pig farming as the result of feeding was investigated using the feed, drinking water or disinfectant prepared in Examples 6 and 7. In particular, the investigation was focused on mortality. A total of 30 piglets were divided into three groups, each including 10 piglets (group A: fed with the feed, group B: fed with the drinking water, and group C: treated with the disinfectant), and an experiment was performed for four weeks. Each group was divided into sub-groups each including 5 piglets, and the sub-groups were classified into a sub-group to which the bacteriophage Esc-COP-7 was applied (sub-group-①) and a sub-group to which the bacteriophage was not applied (sub-group-②). In the present experiment, the target piglets were 20-day-old weaning piglets, and the piglets of the experimental sub-groups were farmed in separate pens placed apart from each other at a certain space interval. The sub-groups were classified and named as shown in Table 3.

TABLE 3

Sub-group classification and expression in pig feeding experiment

| | Sub-group classification and expression | |
|---|---|---|
| Application | Bacteriophage Esc-COP-7 is applied | Bacteriophage is not applied |
| Group fed with feed | A-① | A-② |
| Group fed with drinking water | B-① | B-② |
| Group treated with disinfectant | C-① | C-② |

In the case of provision of the feed, the feed prepared in Example 6 was provided according to a conventional feeding method as classified in Table 3, and the drinking water prepared in Example 7 was provided according to a conventional drinking-water feeding method as classified in Table 3. In the case of disinfection, the disinfection was carried out alternately with the existing disinfection 3 times a week. Disinfection using a typical disinfectant was not performed on the day at which the disinfectant of the present invention was sprayed. The experimental results are shown in Table 4.

TABLE 4

| Group | Mortality (%) |
|---|---|
| A-① | 0 |
| A-② | 60 |
| B-① | 0 |
| B-② | 40 |
| C-① | 0 |
| C-② | 80 |

The above results indicate that the provision of the feed and the drinking water prepared according to the present invention and the disinfection according to the present invention were effective in reducing mortality upon pig farming. Therefore, it is concluded that the composition of the present invention is capable of being effectively applied to improving the results of pig feeding.

While the present invention has been particularly shown and described with reference to exemplary embodiments thereof, those skilled in the art will appreciate that the specific description is only a preferred embodiment, and that the scope of the present invention is not limited thereto. It is therefore intended that the scope of the present invention be defined by the claims appended hereto and their equivalents.

[Accession Number]
Name of Depositary Authority: KCTC
Accession number: KCTC 13130BP
Accession date: 20161017

The invention claimed is:

1. A method for treating a pathogenic *Escherichia coli* infection, the method comprising: administering to an animal other than a human a composition, wherein the composition comprises a Myoviridae bacteriophage Esc-COP-7 which has an ability to specifically kill *Escherichia coli*, the genome represented by the nucleotide sequence of SEQ ID NO: 1, and is deposited as accession number: KCTC 13130BP.

2. The method for treating the pathogenic *Escherichia coli* infection of claim 1, wherein said composition is administered to the animal other than the human as a feed additive, a drinking-water additive, or a disinfectant.

* * * * *

SEQUENCE LISTING

<160> NUMBER OF SEQ ID NOS: 1

<210> SEQ ID NO 1
<211> LENGTH: 54200
<212> TYPE: DNA
<213> ORGANISM: Bacteriophage Esc-COP-7

<400> SEQUENCE: 1

```
gtcttgcgaa tgatggttgc ataaccgact ctcgtggtaa tcaaattaag tgtgctcgta      60
caccaatggt tatcattatg cagagagtgc atgaccaaga tttagttgga tacatacttc     120
```

```
gtggtggctc gtctgataag taccactacc tcaacatccc agccattatt gagaaggggg      180
ttgggagtgc tcagtggtat gacaagttaa ttaagaagca gaactacact catgctatcc      240
cgattcttta tgatttgaat aggaaggaag agaagtctgc attgtggcct tcacgtaaga      300
gtttagattc tctggaggca atgaaagagt ccaacccata cacatacaat tcacagtatg      360
ctggcgaccc atctgcacaa ggccacggcc ttatcaaaga agattggtgg caagagtatg      420
aaccggatgc tttcgacaga agtcgcatag tcagaagttt tattacagcg gatacggcat      480
caactgccaa atcttattct gattattcgg tccttaagca ttgggcgtg actaaagagc       540 gtgatgttta ttgtttagat attatgcttg gtaagtttga actccagaa ctcaagactg       600 ctattatcga cttctggaac aaatgcaaca agttggactt gaagtgtgta ggttgtattc      660
ctcgtgcact gtatatggaa gataaatctg ctggacaatt cttgaaccaa caatttatta      720
gagatgggag tgtccgagtt ttaccgttgc ctcgtgatgg gattaatggt aatgacaagg      780
taactcgatt ccttaacgca atcccatatt tctcacaaaa gagaatattc ttccctgctg      840
gtcatgaaca cattgaccac gttagacgtg aaatacttgg attcacttct ttgggtagtg      900 gtactgagaca cgacgattgt gtcgataacg tttcagatat ggttgcaatc gaattctcag     960
gcccaagtgc caactactcc gcatggatgt aaatatggcg ttatcactc gtttagatgc      1020 ccgctcacgc aagaacaact ccttccagat tcaagatttg gaaggaaaca ttttgtgtgt    1080
gattgaggca gtttctacta cagagagcga ctgtgttaag ttaaagcacg agtcaaatct    1140
gcgactccac acctccgaca acattcaaat tgttaagggt aatggaacta ttctaaggaa    1200
gaaataatga cttccaagaa gaaaaataat ctctctgtta aagttgcaga tgggttagaa    1260
aaccttgtaa caggattggg cggtcaggca gataagtcca cttttaacca gtggaccttc    1320
tcaaacaaga acgcgaacta tcgcgaactt atgaaccgct tccgtgagga ttgggtggca    1380
cagaaagtgt gcacagttat tcctcaagac atgacgcgta agtggcggca tattgattcc    1440
gaagagggac gcaaagcgga taagaaactt cgtatccgta aactgttccg tgaggcgtat    1500
caatgggcca gattgtatgg gacttcattt gttctgctcg acctaaaagg tacgggcaaa    1560
cttgacacac cattgcgact ggataaactt gaagactggt gtattaaatc catgagagtt    1620
attgaccgct cacgcttatt tgccgcaggg actatggttc tggaccccttt gagtcctcac    1680 tatggtttgc cagagtatta cactttggct gggtatcccg gctatatcca ctacactcgc    1740
tttcttcggt tcgagggtac tgaacttccg ctgttcgaat ccaacgaaa catgtggtat     1800 tctgattcgg tacttattcc actgttgaaa acgattgacc aattctacac aactgccgct    1860
gctgctgcca gccttgctca agaagccaca attgatgtgg taactgttga aggcttacaa    1920
tctctgctta catcgccgga aggtgaagct gctgtgatga agcgcttcaa acttatgaag    1980
ctggcaaaga gtatttataa cgtcttaatt ctcgacaata ctgagaagta tgacaccaag    2040
tcaattgcac tatctggtgt gaaagatttg atttgggaat acttgaagat tgtagctgcc    2100
gcagttggta ttccggctac acgtttcctt tctgcatctc cagacggtat gaatgctacg    2160
ggcgaatctg acctcgtaaa ctatatcgac ttgttgactg gcttgcagac ttctgtgttc    2220
gaccctcgtt tagatgtggt agacaagatt gtccaagcgc actttggcat tgaagaatat    2280
aactacgaat ggttagacat cttccctgaa tccaatgttg agaaagcgaa gcgagctaaa    2340
gatttggcat tcgctgttga cctgctggtt aacaacggca ccattaccac ggaagttgca    2400
aacgaagtca tgttccattc aggcgtgttc ggaacttgtg accttggcaa gccaaatcct    2460
```

```
aatcctccta acatccaaaa gggtaacgca agtgaagcaa aaccaaaacc tggttcagct    2520
taacgacgaa gataccgtga atgaagtagt tttgttgaac gacaaggcta ctttaacgac    2580
ccgtcgttta cgtgactctg gcgagatgat tgcagaatgc accatcgctc gtactggcat    2640
catgctgtac aaagcgaaag aacttggtga aattgcaaaa catctggacc cagaatctat    2700
ttgccgtgtt cgtaccaagc cggaagtatt atttgacgaa gcaaccatcg aaggctgtcg    2760
ttcaattccg gtaactatcg gccatccgaa aaatgatgtt aacatcaaga acaacaaaga    2820
actccagaaa gggttcatcg aagggcgtcc agttgcagac ggttcttttct tggctgcatc    2880 aatcgttttg aatgacgagc aagctattcg attagttgat tctggtgttg accaaatctc    2940
cttgggccat aatgccgaac tggctgtatc agaagatgat gaagccgact tcgataaagt    3000
tcgcattatc cctaaccatg ctgcaattgt tgttcgtggt cgtgctcaga ctactcgcat    3060
tggtgactct ggtgaagaga ttgccattgt tgataaggca acctttgatg ttgttgaagc    3120
agagcgtgat gcagcgcttg acaagattag tgtccttgaa cagaaacttg ctgatgcaga    3180
aactgcacga ctatccgatg aagctattca ggctgaggta gacaaacgtg tagttgctcg    3240
tacagcactg cttgttgatg tggcccgtct tggcgacgag ttctccaacc tcgatttctc    3300
cggcaagact gatgcagaaa ttaagttggc tgtagttaat aaattgcatg acaaggattt    3360
cagcgataag agcgaagact atatctccgc ccgtttcgat gcagctcttg aagattgcga    3420
ttccattact ttaggagatg ccctgaatca gtctatgcaa ttcgctgcta agaaagattc    3480
agaagctcgt aaacctaaag tttctatttc cgaagaagct aacaaacgtc gtttagaacg    3540
cttcaactct ttataaggta agacaatgcc aaagcaagat tggtctatta atactggtga    3600
agcatatgca ggtgaacaat acggcctggc taccaccaac tcccagcgcc tgacctacgt    3660
tgccgaagaa gaaatggcaa actttggtct ggctgttgtt caaggcacgg cttctaatca    3720
ggttaaacct ggtattgaat ctgatggtac tgttctgggc attaccatgc gccagattaa    3780
catcgaatct gctactcgtc ctggcgacgg tactgttgca atcaaagttg gctgcctct    3840 gggcgttatg ctgtctggcc caatcatggt caaactggta actgcaatca ccgataaaga    3900
cattggcgta tctgccactg gtcaatttgg tggcgttggt gctggctata ctaaagcaac    3960
caacctgact gccctgcgtt atccggctgc tgctggtgat gttgttccgg tcatgattaa    4020
cgtagtccca aagccgtaac gccacctcca gctcctgcgg tatctgctgt agcaggcact    4080
gtaactgcgg acgcatctgc atctgatgcc actgtaactg tagataaact gtttaagttt    4140
gagaactcta cggcaacaga ttacaacttc gccgttactc ctgctgtagc tggtgtttct    4200
gtggcggcaa acggcactgt gactgtactc agtgcaacga ctacagccac ttctgcgaca    4260
atcaaggcaa ctaataaaac agaatctggt gtaactgcat ctaaagtgat tacgattaag    4320
cctaaacctc ctgcacctac agtatctgct gtagctggag ttgtgaccgc tgatgcgtct    4380
tctgctgatg ccactgtaac tgtagacaag ctgttcaagt ttggtaattc tacagcaaca    4440
gattatgcct acactgttac gcctcctgtg actggcgttt ctgtggctgc aaatggtact    4500
gtaactgttc tgaatgaaac gactactgat acctctgcca cgattaaggc aacaaacaaa    4560
acaacctcca gcgtgactgc aactaaagaa attgctatta cgccgaagtc ttaagttgtg    4620
atggcgcaat taatagttgc gcctcaccaa acaaaacgga ttaatttaca tgcctaagat    4680
gattaaactg gcggacggtt ctgaattcga actgaacgac gctatcaccc gtattcagga    4740
ttctggcact gttgtcctga atgacgacga tgcagtattc tttcaacgcc agcttgagtt    4800
cattgaagct caaacttacg acactctgta tccagaactg gaagctcgtg ctgctttcgg    4860
```

```
tgtggacact actggtggcg ctggcgtaaa cactctgacc taccgttctt acaaccatgt    4920
tggtaaagcc caggtaatta acgcccgtgc aaccgacctg ccgaagtcca gcatttctgg    4980
taaagaatac agcatccctg ttaaatcagt tggtactgca ttcgactacg atattgatga    5040
agtagcgtct gctgctgtta ctggcctacc gctggaaacc cgtaaagcaa atgctgctat    5100
tcgtggttac gaacagtatg ttaactctgc tgcatggtac ggcgataaag ctaacggctt    5160
tgttggcttc ttcgaaaacc cagacattac caaagcaact gttgctgctg gtgctggtgg    5220
ttctaccaag tgggctgaga agactccgac cgaagttatt gccgacctga ccactgctgt    5280
gtctgcaatg tatgcctcta ctctgaaaat catgcgcccg gatgaaatct ggatgcctgt    5340
tgagcatgag cagtacatct tcaacactgc acgttctgag cagtctgata agacgattgg    5400
tcagttcttc attgataaca accagttcat caactcccgc gataaaatca agggtctgaa    5460
cgcaatcaaa ggtcacggcg acgctggttc cgattgcttc gttgttgttt gccgcaatgc    5520
aatgggcaac cgcactttcc gtctgcgtga acctctgccg ctgacctggc aaccggtaca    5580
gcttcatggc ctggtttatg aagttcctgg tcgtggtcgt ttcgctggct ccaagcgat    5640
gtatccggca gcaatctcca tcaactccgg catctgataa atagggcggg actgttctcg    5700
cccataactt aagagaaata gtaatgcaga ttaagaacaa cgaatcacgc aaccttcaat    5760
tcttcttctc taagaaggga aagtctggca aatctgaact ggactttgtt cacattcctg    5820
gcggcgcaac tgtagaaatc gatgatgaaa tctacaaatc tcttacggca tctctgacgg    5880
aagttgaaga actgcgcgaa gaagtggttc cgcttgatga cgagaatatc ggtgcttctg    5940
ttaagaccgg taaagaagct cttgtcatta agagtatta cagcactggc aaaactcgca    6000
aagtcaacct ggttaaagaa gcaatcaaag ctggctctct taccattgtt gaacgtgtga    6060
aagttggtat gcctgacatt gatgccatcc tgactaagaa tggtattgat attaagggca    6120
tgccggaaga cgttaaactg gcactctacg ataagttggc gtaaatgata acactaaccg    6180
atttggttaa acgttatccg gcaatggctg acatgacccc agagcgtttt gatattctag    6240
ttgaagatgc aaaacttatc atggggacaa tcgaatcgcg ttggtgtggg ttttatgacc    6300
cagctatggc atcacttgta gcgcattggt ctgcaacaat tgacgaccta atgcctggtg    6360
atgccgcaat gccagctatg cctgttagtc gtaccgatgt ggacgatgtt caggtagagt    6420
ttagcgaccg aatcatttca acaattccat atgttgaagc tgatttcatg tctactgtgt    6480
acggtcaacg ttacttgcaa tggcggcgaa tggcatttgc tgggccgagg gttagccctg    6540
ggtcacagtt tgattaacc agcgtcgagc attcaaccgc tacacaacca ctcgtatgta    6600
tcttgaggta tatcaagaag gttactacga tgacaaaaat aattggggttg gtgattcata    6660
tgctccaaag aaacccatcc gatgtactcc cataccttat ggtgacaggg attctggcgt    6720
aagcggtcaa tcgcttaaag ctacagaagt cggagagcgc caacctgcat tcatgcaagt    6780
acattcccga actgaaatgc cgatgaagtc tatcctaact atctacggcc ttcgttataa    6840
agttatttct gtttctgact acaaggcagc tggattcttt gaagtcattg ctgcaaagga    6900
gttagagaaa tgatttatga tgaagatatt caggcgatga aggatattgt ggacgtctgt    6960
gttggcgtcc cacgcttctc ttatgagatg cagataaacg cacctcgacc atctgataac    7020
tatgccgcaa taaatgtgt gtcgtcagtt aatccaggct ttgatgaaac tcgaatcgaa    7080
gtacgcgatg gtgaggaggt atttgttacg agagggattc gaatcttaac cttctatatt    7140
ctcttctcac gtcgtgggag tgagtatgtt aagtttgata attccttctt ccgtccagat    7200
```

-continued

```
gttcaggcca tgcttaagag caaaggcttt gcaacactcg acaaaaatcc actgaatctt    7260
gcctcgttaa ctcttgagac gaattgggaa ttccgagaag gaatccaaat caagttcaat    7320
gttctgcgtg aagacgtaat gaatattgga acaatgtctg acgccagtgt tggcggcaaa    7380
ttctatgatg gtggtgaacc catcctaatt aagggaatct aaatggcaat tccaatttcc    7440
gatatcatcc aggtcaacat cgcggtatct ccgaatgctg ttgccgtgga aggttttggt    7500
cctctgctct ttctttcgaa ggagtttaaa cctactgctg ccgaagtagt tcctgttcgt    7560
caatatacga gcatggctgc tgtatctgct gatttcccat ctggtgaaat ctataatgca    7620
gctttagcgt ggttttctca gaaaccgact ccgaagtatt ccttgtgggt gctatcact    7680
catgaagatg ttactccggc aacttctggg tctgtcacgg catcttctgt tgcaactctg    7740
gaaactatca ctgcgttaac caacggtgtg ctgtccgtta acgttgatgg cgtagaccgt    7800
tctaccgccc caatcaactt ctcttcggcc tccgactttg acgctgctac ctctatggca    7860
aatgctgcac tggttgctgc tggtattcca gttaccatgt ccaacaacaa gggcactttc    7920
aaagttgtta ccaagtctgt aggctctggc tctattattg gtaacgtata cggctctgct    7980
gctccagcat tcgagctgga ttccgaatca agtccggtat atgtgcatgg tactgatgaa    8040
gtatctgtag gctctgacct gagcgcaatc ctcaactcaa cgttcgactt cttcttcgtt    8100
gcaatcgacc gcaaatatcg cggcagtgct tctggcaata ttcagatgac tgttgctaaa    8160
tgggcagaag caaacgagaa agtattcggc tgggctgata gcgacccgca gattctggtt    8220
gttggtgcag aatctagctt caaacgagct aaagaacaga acctccagcg taccctgctg    8280
gtatatgatg cctctgacaa tggtgacgag tatccggaga tttctatcct gggccgtgca    8340
tctactgtca acttcaacgt tgcaaactct gcactcgttc tggcatttaa acaaggtccg    8400
gctatcaaga ctgctgacct gtccccgaac cagcttgctg cacttgagcg tgtaaatggt    8460
aacgcattca tcaacgtggg tgggaacact atgttctaca acggcaagat ggctgacggc    8520
acttggttcg ataccgttca gggcgtatct tggctgacct ctaaagttcg tgccaacgtg    8580
ttcaacctgt tctacacctc tacgaccaag attccttgga ccgatactgg tgtggctctg    8640
gtaaaccagc aggttactct ggctctggaa ctggctgtga ccaatggtct gattgctcca    8700
ggttacgaca atgaaggcaa cttctaccct gatggttaca agtcttgtc tactgacatg    8760
gctctgatgc aatctcagaa aggcgctcgt atctgggaag gcacttcctt cattgcaatt    8820
ggctctggcg cattgcaggg tgcagttatc tccggcaact tcgttcagta agggtgcgat    8880
aagtgaatcc aaatagcgtc cgtgttggtg agatatttac gaccaggcac ggagacctaa    8940
ttgttgaaaa atatattaac gccaatgaag ttgttgtaag gttcctatct acaaactctg    9000
taaagataac ctcgtcagga acattcgca aagggctagt taaagacttg tgtgcaccaa    9060
cagtattcgg tgttgggtgt attggtgtcg gaaaatattt atcaagtagc cgaagggtta    9120
aatcttctgc atatatttgc tggcacaaca tgattaaacg ttgctactgc aaggagtacc    9180
aagaaaagta tccttggtat tctgagtgta cagtatctga agaatggttg aactttcaga    9240
attttgcaga gtggtactac gcaaacttta aggaaggatt tgaactggat aaggatatta    9300
aatgctttgg aaataaagtg tactccaaag agacttgtca gtttgtccct cccagcataa    9360
acagaagcca caagtcggcg tacacacttc gcacgcgtgg caagaagact aattttttag    9420
tcggaggtta gtccaattaa gcagtactca ttttataata ccgacctcat tatcgacggt    9480
gctcgtgtag atggttttac ttctggtaac tccatcatca ctgctcgtcg taacgcacct    9540
caacacctgc ctgttattga cgcatatggt aagttggctg tagctactac ggctgacttg    9600
```

```
tctggtacta ttactttccc gcttctgcaa accgcagact ggaacgaaat cctgtacagc  9660
cgtgctcagt taactcaggc aactggcctg tctggtaaca aatctctgtg gcaaccgctc  9720
cagattcaga ttgttgacaa gatgggtgat gtgctggtca atggtgtaaa cggcgctatc  9780
ttgcagcaac ctgcaattca gcgtggtgta tccttcacgt ctaacgtgtg gctatctttt  9840
gtagaacgcc tccagattaa gactggctct tatccggaaa ttggcgttta attggagtaa  9900
gtatggcttg tgaattgctt caacgtgaat tcacaaactc caaggcgaa acggtgctag  9960 tcgttgttcg acaattgtcg gcttcggctg cactgtctct tcacgcggag ttggtaagca  10020
agctaggctc acgagtattt ccattcatcg aaggcaaata taacttcgct gatattattt  10080
acttgatgca gcaagtggag cataccgtat tcacagaact gtttaagcgt gttatcagca  10140
tgcactcgtc catagatgga caagaaatca aacctgcatt gtatgatatg cagttcaatg  10200
gcgaattgat gttgtcttgc catgtctttg ctttcgtgct cgaagcaaac ttccttgatt  10260
ttttcaagca agggctcgaa atcaacgaac agagacgatt ggaggcggag gaagcatcca  10320
agctggcaga gcagaagaat tcgagtccgg agacagttta gtatccctgt tccccgacat  10380
aaaatatttt ctgcatcgtc ctataatcga agacagttct ctctgcaagt tacatgaatt  10440
gcaagatgga acctattcga ttatggactt attgctattc catgacattc tcgatttgcg  10500
taagaaactc gaaccagtag atgaagacaa tggctaatca aaagattta atgaagttga  10560 gcgttaatga attaattgca ttaggctctc aaagcggtct gactttccac gctggtatga  10620
agaagtcgca catggttcaa caacttagtg cgagcgctgc ttcgggatgg ctggatacaa  10680
atgcagaatt aatgggtggg tcgtttgaag atgacagttt aattactgaa tctctgggcg  10740
actcttccat gatttcagac gctgcccaca ttgcacaagt gctttcaagt gcaggctaca  10800
cagaagcatt tcatgcagca atgaatggcc catcacacca tgtagaagct gttcacgcat  10860
acatggaaag gcttggtgtc aacacagacg atgtgtggat gcacatgcca aagccaaatc  10920
cgaacttacc gcaaggtagt ttcaatatgc ttaatgccta catgcgagat actttgcaag  10980
ggcatcaaga tattatgcca gaaatcccag gccactatgc tggtgatatt atggctgagt  11040
actccaccaa ccgtggagat attgccaaat ctatgggcta tcttgctcat atgtatgttg  11100
accgtcaaca atatgacgac ccagaccgct atgcacgaga tgtttatcgt gtagccaaac  11160
gtttagaatc agaattgccg caaaacttcc gtgaagttgc tgctgtatct gcaatgaatg  11220
taggtaataa gtcggggcca agagtttcat acatggattc tcttcctcaa cttggttccg  11280
aatctattgt tggtgatatt caacatcctc gccaaccact taacgcatct ggcctgcctt  11340
taggctctat gggttctgcc attaaagctg aatattcttt atctgcatca ttatctggct  11400
ccccaggttg gtctgatgca agtaaatctt tatatcaaga tgtatctggc gtagttaaat  11460
ctgctgctaa ggtatatgct ggtggttcag agcgagggat gaacgcatat cgcactcaat  11520
cttctgaccg agatttgatt cttgattctg catctcgtta tacagacctt gcagatgctc  11580
gttctggtta tgacaaccta agaaagata ttggtgatga ccctcgttac tctggtgcat  11640
ctattcgtgg cgtactggaa aatgctcacc aatataatga agctgaaatc agtaagactt  11700
tcgaccctgc tgaacgttta agaaatactg gacctactga acttagtaca tccagtgagt  11760
ttacggcaaa tctagatgaa ccgacaagtt ggaactctgc aagggataga agagagtcta  11820
ttgctattgc aaatctcgat agtgctacg ttagacagcc tagttcggtt aagtaccacg  11880
atgcgctcga acaaggtacg caggaatggc ttgattttcg taagcagtat gatattactg  11940
```

-continued

```
gctctactat tggtgattat ttgggccaca accccgcaac caataatagc ccaatacata  12000
caatgggcga aaagattggc ctcacagtaa gaaaggattc accacgagcg cgtgagaact  12060
ttgagcgtgg acatagatta gaggcgtggg ccagacccag ggtaggtgaa cgatatgggg  12120
ttgaaataac tgaaactggt gcaatcacaa acgacgacta tcctggcatg atgtactcgc  12180
ctgatgggtt aattggtgat gatgctttgt gggaacataa agctccaaat aactttaaag  12240
atttggaaac accccaaac tacatggacc agatgcaact tggtatgcat ttgagtggtc  12300
gtagtcgcac actgtttacc caaactgttg gcgaggaatc cagaagtcag tgggttgaag  12360
ccgacccaac gtggtttgaa cgtaacaaga acaagatttt atcctctcaa gcacgtatga  12420
atgctggccg cgagtttatg gaaagctcca accttgaggg caaagacctt gttaatgaaa  12480
cccgcaaagt catgtccggt gatgggattt ggggctatca gactcgtgac catagggaag  12540
gtgagggata cactgctggc aagcgaggga tggctaaata tagtgctgct gctggcactg  12600
ccgatgaccc gtttattggc tcccattctt cctacagtcc agaggcatcc acctctagtt  12660
accaaccaaa ctctgctaca cacgagcaaa attctccgtc tcctgcagga agtggagata  12720
ctggaaatga ctcgatggca ttgtctgtta agaaaggtat ccttgctgct caggaagaga  12780
ataagcaaaa gggtatcagt gcagatgcag actttgatgg caaagctgac tcaatgggtt  12840
ggaatcagga acgattcgat gctgccaatg tggtggaag tggtggtggc ggtggtcgtg  12900
gcggtcactt cacaagtggt ggtaactact tcgatgacta tggtcgtatg ggtggttcct  12960
tagctgctgg cattgctggt ggtagtattg gttcggcatc caacggagtt atgcaagcat  13020
tgatggcaac tcctgccgga cgtatggctg ctgtaggcat tggtgctatt cagattggca  13080
atgaagctgc tgaatacatg aatgacttta tcggcaactc gcttgatgct ggtgttatga  13140
atcctaatga atactcttcc atgtcgcaag gcttggagat gttaggactc aactcacaac  13200
aagcggcacg tctgaatcaa accacacata gtgcctacaa caccatgctt aacggcgacc  13260
ccagcgccgt tgtgaacatc gttcgcggca gtagggggatt gctcaccata ggtgatattc  13320
gtgcgacagg cggcgaccct gtggccctag ctcgcatcat gcaggaaagg ggcaaggagc  13380
gtggctggag tcaggcccgt atcgcaggtg ctgccgaaat ggctggcctg aatgggatgg  13440
cgcgagccta cgaccgcacg gaatacagcc atgagcgagc aggttcggtg gtagaagcgg  13500
gtagaaactc tgactttgcc gaaggtatgg ctcagtcaga aatgttgcag gtggagcgcg  13560
cacagctcct gccagggcat aacgtgccac aaagtgtgtt atctcacggt gctgcactgt  13620
tcgaagctgg aagcactgct gctggtgctg ccaactctgg ttacagccaa gctcgccaag  13680
ttgctgcaaa tgtgtatgac ttcatagcca aggaagaatc tggtgggagg gaatacaaca  13740
aggatggcac acgagttaca agcccaactg gtgctcgtgg aatcatgcag gttcttcctt  13800
ccactgctcg tgacccaggt tatggaatca aaccttctga tggaagtcct gaagaagatg  13860
ctcgtgttgg tcgtgaattg tacgatgcaa tgtacaagcg ttatggtggc gaccacgaga  13920
aagcaatggc tgcttacacg gatggaccca gaactgttga caaggctgtc gataagtttg  13980
ggatggattg gcttaatgct gttccagctc aggctcagaa gcgagttaaa gcatatcgtg  14040
agtgggctaa gtcttccaaa ggcttggatg aaggtgctac agggtttacc cgtaatggaa  14100
tgtcatacgg tcaaacccaa actgttgtta atgtcaagat tgatgctaag gtcaacaacc  14160
agactgcttc tgctacagtg gcaattcctg gtggtcagac tgtgacccaa caaatgaaca  14220
tgaacaacgg tgcgcaacaa agaagataag gagttgggga gaaatcccca gctttccttt  14280
acattagttg aatatgtatt aatttcaata ggtatatcgc aatgccgtgg ctacgcagag  14340
```

```
ttgaagtaat agtttcacgt aaagaagacc caagtattcg gacggtatt   aaatcacatc  14400 gtattgattt tgaagtccgt tctactgttg ggtggcccgc cgatacagca aacataactc  14460
tgtttaactt gtcgttagaa gaagttaagt tcctccaaga caagtcctac ggagatatgt  14520
atattgaaat tcgtgcaggg tatgcagaag atgaacgttc agactctagt ggcgggactt  14580
ctagtggcgg tgctaagaag tttggccaga aggctgaaca gagtgaccgc gtaacaatgt  14640
ctacatcact accaaccatc ttctccggga ttattacaaa cgcagttggt tatagaaagc  14700
ctcctgaaca tgtaacacaa ttgttttgta tttccaaggc atatggtgca tccactgatt  14760
tcaaacagtt gactgcaatc aagcctggaa ccaaactcat tgatgcaatg cgctcaatgt  14820
gttctgacta tgggttcaat accatctcta catttggtgt tgaagattcg gtccttgaaa  14880
cagtgatgcc tcgtgggcgt gtgttccatg acacattctt acacgaattt cgcaacatgc  14940
ttggcgaata caatttgtta tacactgtta caactggtga agtgcaaatc ttcccagata  15000
cctttggtga taaagatgct gtaaacagaa tgtctaaaga cagagagcca gtccagctgg  15060
atgaagactc tgttattggc aaccctgttg ctggaatctg cacctacact ttaaatacat  15120
tcctaaaccc atctttccaa ccaggtatga ttcttgatgt atctccttg  ctcggtaaga  15180 agaagttgct tgctaacggt gtaacttctg tttcagggga aggtattgtt cttaacacag  15240
accagtccgt attccggtgg gctgttgaag acaaatactt tatcatggaa gttgtgcata  15300
aaggctcgac ccactcaacc atttatcaaa catcaatcac tgcaatattg ggtggcaata  15360
caatgatggg tggtaaggaa gctgcgtggc aggaaatgta tgctaacagt ggaatggcaa  15420
tggagtcatt ttaatgtcta tctttgatac cgacctcatt ggtggtgtgt cctccggctt  15480
gaagaatttc agctacgggc atcatccatc tattgtcatg tggtccaatg gacctgcatc  15540
tcagaaggaa gaggaatctg gctgtttgg  tggatttgcg aaatcgcttg agagcttgcc  15600
tattgttggt gaagctgcca ccgaaagttt taactctttt aaatttgatg caatggttag  15660
tgaagaacat gcgtctgaaa caactgtaac caagttccct gttagttctg gcttcatggt  15720
tagtgaccat gttattaacc agaacagggt acttaagctg accgctgttg ctgtcaacat  15780
gcagaactcc tccatgtggt ctgcatctgt acaaggttta tctgttgctt ctggcgcaat  15840
cttcaatagc ccaatcattc ccatccttgg tggaattgct ggtggcgttg cttctgcatt  15900
tgaaacaagc aaccgaatcc agtctaccta cgatttgttt aacagcttcc gtgttacggg  15960
gcagaagtta tacatctcca ccattctggg gccttatttg aattgtgtag taacctcaat  16020
caaaaccaaa catgataaga tgacttctgc aatgttgtca gttgaaatct tgtttgaaga  16080
attgcagaca gttgatgaag atgctcttgc cagcgaagct cgtaaagcaa tggaatcaat  16140
gtctgactat tctgaatttg cgaaggttgc tcaaagtttg ggtatgggtg ttcttggtgg  16200
tgttccactt ccaggactcg gtgctcttgg cactcttcca accaaacagt tatccaactt  16260
gaaaggtaag ttgagtgaac ttgcttctcc actttcttct atcaagggac gtatcctatg  16320
attgagcagg aacatcaagc tctaaaacag attgctgaac ttctgcccac cggatatgtg  16380
aagagtgttc cttacaacat aagtaaggat gtttcgtttg aatttaatgg tgtgacagtt  16440
aaaatgtccg cactatattt aaacgaatac ttaaactgct atatgtttga cctggcttgg  16500
ggagcaacgg ataagatatt tggaatccca attcgttgtg gcattaacat cctcaagcag  16560
tataaaactc cattaccaaa catgtatgca gctaacacag tattccctgg tgaagaagta  16620
acaagctaca gacaactcta cctgttcatt attgacgaga gtgtacttga acgtggctag  16680
```

```
tcataacaat aaccagaatg ctcctgacat taacacaagt tatccaggac acatctacaa    16740
cttcgatgac aaaacacaaa cgtgtgaagt ccagcttgca atcgaaaacc tgtttgtggg    16800
ttatgccgaa gcctatacct tgcagccgaa acaaaggttg cagggcgttc ctgtgcagtt    16860
tattcagggc ggtggctgga gtttaaccca ccctgttccc gatggtacac catgctatgt    16920
tcatttctca caacgaggaa tagaccattg gttgtcacag aacaaagaca gtgctggctt    16980
aataaatggg cgtcctgctc ctgagtttag ccaattgttt tcccacaatg ctgctgtatg    17040
tactattggg actcaacctt tgaccaaagt tattccagga tttaatggtg gagtagcaga    17100
actgcgcaat gcagacagaa gccaaagact aacactgcac ggtgacggtt taattgaaat    17160
cattactggc gctgcgaaga ttcaaatcac aaaagattcg gagattcttg ttgaagttac    17220
gtcgcaagct acagttaaag cgccgcagat tacattggat ggcgacacga ccgttacaaa    17280
atccttaaca gtgatgggtg gcatggctgt atctggcact aaagatggct ctactgcaac    17340
gttcactggt aactttaaga tggatggtaa catggttcaa actggttccc tcactcttaa    17400
tggtattaag gttgatggtc acactcacac taacccagaa ggcggcgagg ttgggccgat    17460
gaaataatgg ctggaaattt agctcttgat tcaaaccacg acattattat tgggcgtgga    17520
acaacccgta tttcaggtgc tgctcaagtt gctcaattgg ttaagtgcag attgctgaca    17580
atattcggcg aatggaagct cgacaattcg ttgggcttac cgtggttcga agcaatcttt    17640
accaagcaag ttcgtccttc ggatattgag gctgcaatag ccaacatcat tcgagggact    17700
gctggtgttc agcaactgct ttccatagat attgatgcag actaccgaga cagaaaactt    17760
ggaatctcct tcactgcatt gtctgattat ggcaacatta cggaattctt aacatggcaa    17820
caatccaata cggcgtaaca gagaatggct ttgttcgcaa gcctgtggcc gacgttgtag    17880
ctaacctcaa taacaaattt attgccgcat ttggttccaa ctttgacata agtccagaat    17940
cccctgatgg gcaatatatc ggaatcatgg ccgacgaaat agcctcgtgc tgggaacagg    18000
ccgaacaagt gtttaacgcc ttccgtcctg gtgctgtatc tggtattggg ctggacaaca    18060
tttgcgaatt aacaaacact gttcgatatg ttgacaagcc ttcacaggca actgttttgt    18120
gcagtggcga ttcaggtact gttgtacctg ctggctctgt tgtaactgac ggaaccatgc    18180
gcttcactct tgatacagac gtaacgctac caggtgacgt aactgttatc gcagaagaag    18240
ttggtgagta ttacattgca ccaaactcca tcaataaaat tgtaactcct gttgctggtt    18300
ggacttctgt caacaacgaa gcggctggag aaactggcat taactatgaa ccagacccac    18360
aactccgtgc acgtcgagaa agaactacgg cagtcagtag cacagccacg gtcgaagcaa    18420
tctatgcttc actcgctgac ctcgatattg attacattcg tgttcgtgat aatgataccg    18480 gctctccctat tggcaatcag ccttcgggca ctgtatttgt tgtagttgat ggcggcacta    18540
gcaatgatat tgcccgtcga atctacaatg ccaaaactgg tggcgtccct actcatggcg    18600
atattacaat cactgtggca gactcaaaag gctatccgca cgatattcat ttcagccgac    18660
caacttacac agacatttat gtcaaaggta cgttccgtcg ccgtgcaaat gccaacttga    18720
gttctaacga tgctattcgt caattgaccg aagcaactgt taactacctc aactccctgc    18780
aaccaggtca gagtgtggta tggtccaaca tgtttgctcc aatcatggct gcaacacagt    18840
cgcttgaaat tgattccctg tttattggta ttgctccaaa cccaactgga acagcaacca    18900
ttgatttgaa tattgacaag cgtgctcgtg gcgttgctgc aaacataact tacacagatg    18960
tgacagtata atatgctgg taaacatggc ttagacatgc tgctttcgca gtatgcactt    19020 tcaccaaaact tacgcaaata tatctccatc ttcttggaag agtttgcaga agttaagaag    19080
```

```
gccatgactg actcaatcaa gtacagatac ttagcagact cattcggcat catggttgac   19140
gaccttgcat atcttgtagg ggcttctcgt gtaatacatg gtgccgcagc acttgggtac   19200
tttggcttct atgccaaccc aggtgcattc tctgctggtg atgataataa cccaaatgtt   19260
ggtggtattc tgaaatcaga ttacgacagg gactctgggg actttgttcg aacagatgca   19320
cagttgaagg ctgcaatacg tgcccgaatc attaagataa ctggcaactg cactatcgaa   19380
caaatcatca cgtacattga gttagttgtg ggaagggaac tgaaacttca aatcatcgaa   19440
ggatttcaga caatggatta tgttgttcat gagatgttgt ctgtacctga gaaagttctt   19500
atggcgcaca tgcttccaaa ctttaaacct gttggggtta gtattaccct caaagatgct   19560
ggaggcaata ttgccttggt ttatggttcc aaagattatc ctccggagaa ataatgactc   19620
aacgtcttaa gtttaatttt ccctgggcgc aaggtggtga agttgaagac ccagacttgg   19680
acaccactgc gccaagtttt atcaaagaca gatatgccga cgtaggttgg aagttgaga   19740
agccacctaa tgagtggcaa aacttcttgt cgcagattag tgacttgaag attatctcac   19800
tcctgtttag tggtatcgct gagtttgact ccagtgtaac ttatcaggtt ggggcagtgt   19860
cttcacttga tggtgttgtt cgtgtctaca ctcccaaagg ttgggaagag gtattggacc   19920
tcaaaaaggt tgagtatctt aacaacgtaa ataacttaaa gtctatttac gatggccact   19980
tggctgcaac caatccacat aaagagactg tagacaccat cacggacaaa acttataaca   20040
agttcgccat agataatgcc tttgggagta agacagaccc aagaactatt gtgtatcaca   20100
agctgcaaac tggccgtgta caccaagaaa ctccgcaaca gcttgggaca ctgccaacat   20160
ctggtggcaa gttctctggc cctgtgtcgc ttttaagtgg tatgaagttt ggaacagaca   20220
tctcaatccg aatgaatacc ggtaacggca gaattgagat gcgcgctggc aacaagattc   20280
tgtccattga tgcactcggc aatgttctgt ggagtatagt tggtggtgca gaatatccag   20340
tgatgaccga actgaactac tcagaatttc agattgctg gggaaacagg ttcgcacttc   20400
ctcaaccata cctcgacatg aacatgaaaa catctatcaa cgatgccatg tcagttcgtg   20460
ggtggaccat caatacgtca gatgctccag tgtttcatcc caaaggtggg attaaagttg   20520
atgacaacac aataaccttt gaaggttttg atgttagctg cccaacgtca atcatcatgt   20580
atggaagaga tgctgccgga aatcttatcc ccgcaaggtc tataaaagct ccgtctgccg   20640
gatacacctc aatggaaact ctcctgacaa acatgggatt cacctctgct gtttgggttg   20700
agagaattac ctgttatcca actcttaccg catatcaaca atcaatgtta gtgaggccat   20760
aatggcaatt cgtcctaaac tgaaccgagt ctggacttca aacaactctg tcgcaagacg   20820
tgacccaggg gatgaaaaat atctcaaggg ttgggttgcg gagattccaa cctatcaggt   20880
tcttaactac ctgcaataca agattgacac cacaatgctt gcacaagcag aacgtggaat   20940
ctttgagtgg ggcagtgatg taagttatgg cgttggtagt ttggcttggg acgaaacaaa   21000
caaaacgatt tatgtttgta ctgttgccag tcctagcaaa acactacgcc caagcgagaa   21060
ctctgcacag tggagtccaa gctccattca gtttctcgt gcaaattacg actcaattgt   21120
tgcagcaatc aatgcgcaca ttgcagacgt aacctcaaac ccgcacaaag taactgctgc   21180
acaaatcggt gcatacaaca gcccgaact tgatgatatt gttgccaact atcgtgcact   21240
ggttcaagca cacgtaacgg attacaacaa cccacacaaa ctaactgctg ttcaagttgg   21300
tgctgttcct gtaaccggtg gaacgtatac cggaccagtg actgtgccaa ctgcatactt   21360
caatgagtcc aaaactgcac aattgttgca agacaatggg ttgtggctga gaatggtag    21420
```

```
ctatctgttg ggcattaatg gcacaaccgg atttgctgaa acaggtactg cggcaagtaa    21480
gtctaagatt gtaacagagt tgagctttcc tgacttgaaa gctgcacgag agcctgaata    21540
tgcggtagaa gcgccacaat atgaaatggc actaataggt tctgtaaaca tacttcgtgg    21600
cacaggaaca ttcagtaccg gagactccga gcctatgtac ttggcatcat ctgggaatgc    21660
tttaacattc gacagctccc aaccctccc atcgcagtcc ttccatgcct cttcacaact    21720
tcctgctagc tcaggtatta cggtctgtgc cgatgttatg aaggtgtcac agtctgatac    21780
aagtgatggc aactggcagc taagtttcgg catcgcagat ttcaatatca ctattgggta    21840
caatgggtat acgaccatta ggtacaggaa cctagcagga gctattgctg taatatatga    21900
tggagtaatc tcccaagatt tgaaaactgt gggtgtgtgg aacaggttgt cggcaacact    21960
ttctggaagc actatgaagg tgtttgtaaa tggcgtactg ctattctcca gagagcaaga    22020
agtgggtgtt gcagttggga gagcgccatt tataactaaa tgggctatgg ttggggctac    22080
cacaagctcc agaatgtcta ttaggtcttt taggttgtgg aactcagcac taacagataa    22140
acaagtttca actttatagg attcaaaatg gctaaaggtt attctttaga tgcgttggtt    22200
caagagcact acatgaagtc ccgtaccaac ctggataata caaacttaga cactctcaca    22260
ggaattgaca gtgttggggt gtattaccaa tcagccaatg ctcttgccac ggttgcaaac    22320 aactaccta ggggtgctca ggcaggaacc cttgaggtat tgccacacgg cgccaacgtg    22380
gctggcaggg tgatgcaaag atatacagta tacaacacat tgcgttgctg gattcgcagc    22440
cagaactact ccgcagacaa tgcatcgttt gggaattggg tggaacttat aaatgcaaac    22500
aacatttaca acgccatcta cccaattggt attgtattgc agtttgacaa tgccaccaac    22560
ccgaacaaca tgttcacagg aactgtgtgg gaacaaatca cagatggtcg ggctgtccgt    22620
gctgcaactt ctgctgaggc tgggactgct gatgggcaga ttggttcaac agctgggtct    22680
gatacagcca acattgctgt aaccaaccta ccaggccaca cacgggat gcagaaccac    22740 acccacggta tctcagacca ctcccactca atggcccaca cccacacaat caaccacgac    22800
cacggtgcag taaacactgg ttcggctggt gctcacacgc acagcctaag cggcactact    22860
agctctaatg tggtcacca acacatagaa ggctcgccgt ttactggcga cactaacttt    22920
ggtactacct caagctccag aaggaataat atcaaagact ggctctataa tccatcatcc    22980
acatacccac tgacctcgtc tgctggtgct cacacacaca gcattagcgg aactgccaac    23040
tctgagggtg ctcacacgca ctctgtagac ttgccgaact tctctggtac tagcggggc    23100 cccagcgaag gttgggtagg caatacgtcg ctaaccacct gggggcctag caacaacacc    23160
actacctcaa ctggcgacgg tacggcgctt cttgtgcgta acttgtccca ttactatgcc    23220
ttctggaaac gggtggctta aggaaataaa tggaacgttt atccattcag atgtttctcg    23280
acctcatgca ccaatatggc gtttggcatg gattgctggc tggcctgacg gctctaatcc    23340
gtggggcata tgagagtgag ggtttaagca aggcgttgct ggatgcgacg ctatgcagct    23400
taatcggcct gtttgcattt caggtcgctg gcacatttga gactttcacg actaacgtca    23460
ctatgcagtt ggttctggct atcgtgattg gtgtcatcgg tgctaacctc attattacaa    23520
ctgtcaggga agtttctct ggcgcaatca acaacttaa tcctttgacg tggttcaaga    23580
aggcacgatg aaatgataag gaactcgaat gctatcattc aaagttcttg cacttctgac    23640
agctttagtt cacatcaacg ccccagcttc ggttggggca gtgaattctg ctattacaga    23700
ttttgcaagt cattcctatt taaatggaag tctaaaacta tcttcttcac aacgcaaaga    23760
gctagaatgc tatactaaag taatctggta cgaagctcgt ggtgaagata aacatggaaa    23820
```

```
gattctggta gctaatgtcg tccgtaatag aacagagttc gggaagccat tcgctaacac  23880
cgtttgtaat gttgtctatc aacgcaatca atttgcatgg acacgagaag caaagaagaa  23940
gaatgctcaa tggaagcatg tagcaaagat taactatgcc acagaacaac aacaagttct  24000
ggacaccatt aatgttgcaa tctcttttgt actatttaat caaccctctg tcaccaaagc  24060
aactcacttt tgtacagcat cagagaagtg caacttcaag aatgtcaaag gtctgggccg  24120
ctatggtgga cataaattct atgagtatct aggaaatctg taatggctta cactaccttt  24180
tcacaaacca agaataacca actattagaa ccaatgttct ttggtcagaa cgttaacgtt  24240
gctcgatatg accaacagaa gtacagcatc ttcgagaagt taattgaaaa gcagttatct  24300
ttcttttggc gacctgaaga ggttgatgtt agccaggaca gaattgacta tgctggtctt  24360
cctgagtgtg agaaacacat cttcaccagt aatttacgat accaaatcct acttgattcc  24420
attcagggac gtggaccaac tacagttctg ctaccaattg tgagcattcc tgaactggaa  24480
acttggattg aaacttggtc tttctcagag acaattcact cccgttctta cactcatatt  24540
atccgtaata tcgtcacaga cccaagcgtc atctttgatg aaattgtaga gaatgagcat  24600
attcgttctc gtgcaattgg catctctcag tattacgacg agcttcagca tcttacttcc  24660
atgtggcatc tgcatgaaga tgaagtagac cttcgtgagc ttaagaagaa gctgtattta  24720
tgcctcatgt ccatcaatgc actggaagca attcgcttct atgttagctt tgcttgctca  24780
tttgccttcg ctgaacgtaa gttaatggaa ggaaatgcca agattattcg cttaattgct  24840
cgtgatgaag cactccattt gactggaact caacacatgc tgaaccttct tgcaagtggt  24900
gttgatgacc cagaaatggc cgaaattgct aaagaatgcc gccaagaatg ccaactcatg  24960
ttcgaaaatg tgggcccaaca agagaaagat tgggctgatt attttgttcaa agatggctca  25020 atgattggct taaacaagca aattttgtcc ggatatgtgg aatatatcac gaatattcgt  25080
atgcaagcag ttggattaga tgctccattc aaaggtgcga ctaacccgat tccttggatt  25140
aatgcatggt tgaattcgga tgctgtacaa gtggctccac aggaaacaga gattagttcg  25200
tatctcgtgg gacaaattga tgccgaagtt gacaccgatg ctctgggtgg atttgaatta  25260
tgattggata cggtgaaggc tgacgttcgt cagttaatat gcgagaagag attcgatgcg  25320
ttagcgtcgt ttctctttaa gctaggataa aataagtaag ttaaatatta cttattccca  25380
atattgctac aatattaaga gtaatattag gaatgcgtaa agttcaaaac caaatggtac  25440
gtggtcggtc aactgtatct ccttcggaga aggtacttgg accaatcttc gttcacggtc  25500
ggtcgactgt atctcgccga aatttgttcg aacagttgtc tgactatgaa tgataaattt  25560
tttttatata atttttttttt tttttttatt tcgaatattg tttcaatatt aacgagacta  25620
gaattgttac gatattggag actcgaattt gttcgatatt aacgagacta gaattgtggc  25680
aattgctcac tttgttcgcc tatattataa ttttatttt gagccagcgg ggaggggaag  25740
cccaacgtcc tatcggactt aaaatacggt ccctacccca acttttttcta cagcctatcg  25800 gctttcaaac aacaccaagt taggtagtgg gtcaaggtca aaggcaatca gagcacgctg  25860
ttgtaacgag ctagtcttac cattagttgg ttgtgattat gaataggcta cgcaagtcta  25920
atccgtttca gttaaatcat aatcaattgg agacttatca tgactaacga agaataccgt  25980
gcactggctg ctgatggcgc tcgcttgaaa gaagaaggcc aaggttggaa agatgtgctc  26040
gatacgatgg accgttgcaa ccagatggta gatgaaatca cctccgctac acaatccgaa  26100
actaaaaccg aaactaaatt ggagactcgc aaaatgacaa ctatctcaac tcaaactatc  26160
```

```
aaatccgttg tccctgctat cactgctctg gtatatcgtg ctaaagagaa acagaactac   26220
atgcagcctc agacctgtgc tattgctgct cttgcaatct ttaagatgat gacgtccttc   26280
actcgtgatg atgttgttcc tgcaatctca atggttgaac tggcttctgc ttctattgct   26340
gatgccaacc gttacaacaa cgatttgaaa gcaatgcact atgttgaccc agctatcaac   26400
ttgattggtc tggctaagca ctttggcttc atcaccatga acgaagacaa atcgttccaa   26460
caaactgatg catgggttga actggttaca accaaagata cctcagttcc attcactgag   26520
cgtgttacca ctgaatctcg tcgcaagcct ttcgttaaag gtggcaaagt taagccatcc   26580
aagactctga agctgcaat cgaattcctg caagataccg agtaccatgt ggagactgag   26640
atggttcgca tcattcagtc tatgattgaa caacgtacct acggtggctt gcagatgcca   26700
gaagcaatcc agactgaact ccatgtttgg aacaatgctg tagcaatgat gactcaggat   26760
acactctatt ctgactactt tgctgataac cgtggtcgtc tgtatcatgt agcatgtgct   26820
ggtcctaacc cacaatcatc tgactttgct cgttgcttgt attctcacaa tgttgagaac   26880
atcgttaaga gtttaacga agatggttcc actaccattg catacaacat gttcatggct   26940
gagctggaag atatttctgg tggtgaatgg tgcagtgcta agcgtttaac ttatgttgca   27000
tcaaatccag ctggttcact tgctcgcatg atgaacatgc ctaaagctga acgtccttcc   27060
aagccattca cttatgttcg tctggctctg gattggttca agtttgagac tacaggtgag   27120
tgtgattctc gtgtaggctt tggattagat gctaaatgtt ctggtactca atatctggca   27180
ttcattgctg gtaacatgga aatggctcgt gcaacaggtc tggttgattc tgatactaaa   27240
gcatctgacc cataccagtt gagtcttcgt gaactgttga agctgctgga taagtcttca   27300
atgaagccat ctcctgaaat catggatgaa ttcttgaatc cgaaagctgg tcgtagtttt   27360
atcaagactc catacatggc tatccaatat ggtggtggta agctgcatt aactggttct   27420 tctgacttca ttgcatacat gacagaagct ctccagattc ctatggagaa agctgaggca   27480
tttgctgaac tttgtgtaga agcaattcat aacgcattgg gtgctaagat taacatgttc   27540
attgagaaag ctgctgatgc tgcatataac cgttgtgttg aactcaacaa agagtacatc   27600
acttataagc acactgatgg tcaagttgta atgaagcctt gcttcccatc tcgtgaaatc   27660
tgtgaggcat tcagcattcg tgttgattct caaactcgtg ttatctttgg tcagattcag   27720
gaagagaaac cttggaccat tcgtgagtcc aatccaacta agaagaatt caagcgtact   27780 ttcgttgtta actacattca aggcattgat gcacttgttg ctcgtactgt tgcagttaaa   27840
gctaaagaag ctggtcttcg tggcttcact tcaatccatg attgtttccg ttgctgctta   27900
gctgatgctc ctaagatgat ggatgtaatt cgtgcagcat atgttgaaat cttcgtaacc   27960
aacaatcagt ttgagaatct gtctaagcaa cttggtggca ttcagatgta tcatgagaat   28020
atcgtaactg aagagcttct gatgagcgaa cacgcttact acttctgtca ataactcgct   28080
tcgctcgtgg gctgtcatcg aaaggtgatg gcccttcctt tattctttat taattaaatc   28140
ctttaattcc caatattcaa gcaatattgc tgcatgtaat attgtttcaa tattcgacat   28200
tagttggata tgaagtaaaa gaatacggag aaatcttccg catgtcatgt tgaatcattc   28260
tagaaacatt cagcatgtca gctttgagtt acagtgttgt aatgatgtgg caatcattga   28320
actccctagg taggccacct acagttccag caaccatgac acagagtagg aatatctatt   28380
cgaaactttg acttcattgt agtttggtgt gcttcatcgt gagaaaggtt gtgataactt   28440
tcgtaagcaa ataaggcatg ttcaattgcg acaatattgc tccatctcct attatcaagg   28500
cccacccaca agccgggaga taactttgat aatattggaa cttttggaca tgctcctttc   28560
```

```
tttcaatcag aattcgaaag aagagaagaa gtcggacaaa gcatcgaatt taatctcgta    28620 gcccgcccg  attttgagca acaaatattg tggcaatatt gtcgcagtat ggcatgtaaa    28680
tattgctaca aattggcatg ttggaatgtg gcagaattgt tagaggacta atcacctcga    28740
agatacaatc gtctaccaat ctggcatgtt aattttgtaa cagtatttgt gccaatttcg    28800
catgtagtat ttaacccaat attcttgcaa cccgcatgaa tactggcttc cagccaagcg    28860
aaggctttat catcgcatgt aatattgtga caatattggg ataaaaccct ttatttaatt    28920
agttttatta tgctgtacat ggtcggtttt ccgtacctgc tacgccactt cttgatgtgc    28980
caaatacatt ccaagatagg tgtaaacctg taattaatga tgcatgtttg attgtgacaa    29040
aattcgtcta tttggcagat gaattagttg caattaagca tgttcattta tcattagttg    29100
catgtgaata agaccaaatc tctgtaaatt ctgctgaaat tgtgtgacag attttagaga    29160
gattatgtct ccaagctaat cattgtagtt ttcggcactt gttgtgtcac atactcccta    29220
caactttaag gtggattgag gtaagacaag acctccacaa tcgttctgta gggagttttc    29280
ctttaacttt ggagaataaa atggatactg tgattaaagc tgcttacttc aaagacctgc    29340
cagatggaca aatctttact gttcgttctg tgaagtggat taaagtaaat gagtcagata    29400
agtacaatgc tgtaaagttc tttgattcaa gtaaggcatg tacttttagc gacaatattg    29460
ttgtcaatat tgaaatcgaa ttggagccag atggttcaaa tgatgaaatc attctgcgta    29520
aaactgttgg atacactaaa ggattctgaa atgaattatg cactgtatca ttatataagc    29580
aggactggac ttgttcgtca tgctttggtc aacattaaaa ctaaagatgt gttgttggcc    29640
gatatgtcaa tccatggaaa caacttagtg tggaagcgtg ctgcaaatcc tagacatgtt    29700
tggcttgtaa tccagtccga caaatatcac aaagttgttg caatggccaa tcgcccagag    29760
cacatagtac cgaggaaata aacatggact tcatcgtcta ctttaagtta aatggtgtag    29820
agcaacgttt gtacttcaat tctttacttc gtttgcaaca gtgggcggag aagtttgttg    29880
gttatgactt tgactacatc aatgcatgta cacctgatga acatgaggaa atcgtgttca    29940
gtggattaaa tcagattctg gaggctaagt gaagagcaaa tatgaaaatc tgctactaag    30000
aactagtggt gggatgctca tactgaccac acctgaatac catttcccaa aggtttactc    30060
cgaagaattt aaatcctggt tcccagcaaa tctaaagaca cgatggctta agattgtgt     30120 acttgttggg aaaaatgtaa agttaaggaa cagatgatga acgaccagca attcaacact    30180
ttaatgcaac aattgaatca tcaagaactt atggatgcca tcaaaggtaa aaagccagta    30240
gagcgaccct accgcaaaat tgataaccat atgccaacaa ttattgcatg tgttggattc    30300
ttgattgttc tctacttcct ggtgaaataa tgtcgattat caagaaatta gtattctgtg    30360
ttctgatgtt ccctttggtg ctgctcgttg tgggcagctt cataatctaa actaaggtaa    30420
ttaaatggct tctttactcg aattctcaaa tattgcaaat gttgctaaga attccattcc    30480
tgcaaatact gatgtaattg catatatgcg tgttgatgta agtctgttgg cttttgtaat    30540
ggaccacatc aaccttgttg aagagcagtt gtctcaagcc aatgaaacaa ttgacactct    30600
tcgtaaactt cgtgaggcag aacaaaacgc ctacgatgaa ttgatggagc agaagaacaa    30660
gctccaagaa cagttggcag atgcacttca acaaattgaa gatatgaagc cagcaccaac    30720
caaacaataa gacttaggag ttattatggc tactagaaca ggcatgatga ttgtcccaag    30780
ccgtaataac tctttaagcg gctttacacc atataaaatc tacgaagtga tttctggcac    30840
tggtgaagca aacctgtcag aagttgcttt gaagttgggc cgtatggtcc actccgaaat    30900
```

```
ctcctgtaac gtagttgatg atgaaggtaa aatccgtttt gtaacaatgg atttctttcg    30960
tgaatttaat cttaaatctg aaatcggtgt tttatatcat gaaatttaaa tgtgttgctt    31020
caaccaaaga ctatgttcca gttggcttca ttgttgaggg tgaagctatt tcgcctttgg    31080
aatttaaagt aaccaaatct gctgaaagca tttctccagc attccgtaaa ggtgctgtag    31140
ttccgatgaa tggtgcattc tggacatggc agcgtgacca tgaagcagaa tttgcggata    31200
tttgtgaaca aggttctctt caataatttc ctcaaccact tttgtaatga gagtggttgc    31260
tgaatattat taattaactt ggagtgtatg aaatggccaa attcaaatgt gtaaagagtt    31320
ctgaatacgt tccagaagga acaattcttg agggtgtcca agaaaggggc agactcgtac    31380
tgaccaagcc gtccgagctt cttgggtttg acggaaatcc gagattccgt gagggtgatg    31440
acttgccaat ggtaggtgtt ttatggactt gggaagagat taaagagcaa gtgaaacaac    31500
gtacacgttt acagcgtgac ccagccacag gtcgcttttt gccagcatat ttgaaagttg    31560
gtgacttagt ttacactcgt gactttgctt ttgacatttg cccaagcaaa gcgtatgaag    31620
ttcttgccac cagcttgtct ggtcctagag taatattcgg tgcacttgag ccaatccagt    31680
taaccggaac tcagttttgtc atcaaagacg aatctggttg caatcgaatc ttcaatcttg    31740
aaggcggttt atccaaatgg gagaaggtga agcgtgggta agaattatat cgaaatgttt    31800
aagcgattgt ctgtaaatgg gcaggagttc ttgttaaacg atgcaagaca agacattgaa    31860
ttgtctgaca agtattctta ttttgcccaa aagacaattg tgaagtggac attctcttac    31920
atgtccgccg gtattccagg agaaacgctc gtaattagcg gttctggaga ttcagtttta    31980
acagctttgg agaagctaaa gcaatgaata agaattcagt cttgcgttat gttggtaaaa    32040
caaactacaa ctttaccaac ggtaagaaat ataaaatcgt cgcaggtcgt ggtgacggag    32100
ttcctcgcaa caacggtaca ctcggtgcgt atattcaatc tcctttgggt tttgtcgtta    32160
atgacgataa ccgcaattta tgttatcgta cattctccga taattgggaa cttgtaaaag    32220
attctggtga agttagttgg tataaacctg aatcaaacat cgacccaatt cctatttcca    32280
aatctatgtg attaacaatg ggcatctctt gtaggtgtcc atgattaatc taacattagt    32340
tggatttgaa gagagacaaa gctattccgt ggttagcaat gtcactgaaa cttaaactgt    32400
aattaactta agagaatctt aatcatggca caatattcag atgtaaacac tggcattatc    32460
ggtcctaacg gcttcaagaa agacccaaaa catcctgaca ttcgtggacg tattaacgtt    32520
gacggaatct ggtattgggt atctggctgg aataagcaag caaatggtaa tgagtttacc    32580
tcacttgcat taaccatcat gacccaagaa caagttgatg aaatgatgcg taagcgtaaa    32640
gagaaggcta aagccaaagc tcaaccccaa gctgccgctc aacagcaaca gccacgtcag    32700
cagccaactc agcaacagca agctcctgct cagcaacaag ctccgcagtc gtctggatac    32760
aatccaaatg aaccgcagga ctttgactcg gacattccgt tctaatggag atgccctatg    32820 aaaatttttat gttttatagg ctacataat tgggagattt ctcatacaaa cgattatgta    32880 acctttggg tatgcaagaa ctgtgcagca atgcgtgagg aatatcatgg acaataaggt    32940
tgtcgaatta cctgccaatt tggttaaagc tggcgatgtt gtatttcatg atggtagagg    33000
gtatccgatt gtacacatca acagacttag tgatgtagtt cagctacaac acgctggcgg    33060
attctttaat tttgagttgg gccgtatagt tagagtattg gaaaaacgtc ccactacaga    33120
atcttttaca aagcctacca caacccgtgc agtattggcg catgaagtac gacctggaaa    33180
catcttatct tacggaatca gattcttga gataaaggaa gttaaagacc ttggggaaat    33240
acctgaaaat gtggttcgat taacccatgt aacaggatac tttgactttt cacccaaccg    33300
```

```
catagtccac attgttaata cgccaccagc ttcggaaacc ccaacaattg agttcccaaa   33360
ccaaataaat ccagtattcc ttcctgtgga gagcaacatg gaaacattaa atattcaaaa   33420
tgcaattgaa gcacaacgta ttcttctgca aaagctggag caaatgcttg atttaaccca   33480
tcttccccca acagaagatg gcaagatggc aattggcaat gcatcaattc gcgtggacaa   33540
ggcaacagtt gttaaggccg cacgcgatga atgaaagct gccgcaagca aatccgcaga    33600
gcttatcaag aagctgtaat taacagaggt cattccactt cgagtggcct cgattaatta   33660
ttaccggagc atttatgaaa actttataca ttgcactaac aattcttttc ggagtattcg   33720
cattcaaatc ggaagcgtct gttcgaaact ttcagtgtgg cggatataaa atgtccgttg   33780
aaacaattac aatgagccag ccactcattg caacaatttc tttgcacgaa ggtacttgga   33840
ttgagattcc agataacgga aatccaaacc caatgtcaac agtgttctat aacacacaga   33900
gcagcaagct ggctttagtt ggtgttgacg ctgaggaacg tttagtgctg cagatttatc   33960
gtaacattga cttctttcat gccaaatttc cattgttatc aacctattgt aaggaagtta   34020
aatgacatca tctgaattta ccattgatgg agtaccgtac ttacttgaat ccagttgcga   34080
atatcgtcac tggtcagtaa ttcgtgaccg agtagttaaa ttcttggagc gagtagggaa   34140
agatgcagct attctgacta cagccacagt agaagggaca accgaaatca atcgggagct   34200
tgtatctttt aaattaacca tcaacccaac aggaaatcca ttccgtgaaa gttgaagaat   34260
tggctgacca ccttgaggca gcaaaacaag agcttgcaac tcactcagaa cgtgttgaaa   34320
cactgaaaga gcaaggttca acaacagaag aaatccagct atttacagat aatatctggt   34380
tttcaatgaa tcgtgcacag tttattaaga ttcaggaaga ccgccttgct gaacttgaaa   34440
agcgtgtgaa gacacttgag aacttgctcg taacattgca agaaactctg gaccaggagt   34500
tgaaaaatgt ctaacgttaa gctaggccaa cgctcccttg accgactcaa aggtgtaaat   34560
ccttcattgg tggcagtttt caagcgtgca tgtgaaacaa tgccgtttga tgtaactgtt   34620
cttgaaggat tgcgcactta tgagcgtcaa caagagcttt taaagcaggg tgcaaccaaa   34680
gtttcagtta gccgacacat gtcaggcaat gctttggaca ttgcaccata tccgattgac   34740
tggaatgacc ttgagcgatt caaagtttta gctcatcaca tgttcaaagc tgcaaaagag   34800
cttggaatta ccattcgttg gggagcgacg tggctatccc actacgaaga acctattaaa   34860
tgggctaaat tcttggatgc accacatttc gaactcccga ataatccaa ggttcgacaa    34920 atatctaagg tattgccctg aaacgggcaa ccttattcgg acctgtacca ccagcccaaa   34980
agcacggacg ggagacgttg ctgggtatgt ttgtggtgac ggatatttaa gaatatctgt   35040
cgaaggaaca aaatggaagg cgcaccaaat agtgttttgg atgcatcacg ggtatatccc   35100
aaaggttatt gaccatattg ataggaatat tctaaacaat aggattgaaa atcttcgtga   35160
tgtgtctaca aaacagaact tgatgaacgt ggggggtgtcg acctccaaca cctctggata   35220
caaaggtgtc cacaaaagca gtagaggcaa gtacgttgcc aggatatccg agaatggtgt   35280
aagaagatgc cttggcactt tcaatactcc agaagatgcg gcaagggcat acaatgctgc   35340
tgcacttagg tatcatggcg agtttgcata cataaacaaa atctagtaaa tggagcatcc   35400
gatggaaaac caaattattc aagcagtaac aaacctcaag tcctggcgta gagatgaaac   35460
cttattggtt cgtttctaca caggcgaaac taattctgaa tttgtagatg cgtggattga   35520
tggactagca tggcgccttt atgatttcag catgtccgaa tatttgcatg aagaatacgg   35580
cattgagtac cctgcaacag gaacttatga cataattgaa tcaagagatg aagatgttac   35640
```

```
agaggtttgc tttgttgatg gtatgttcag cctacgcaag tatgacaaat tcaatgaact   35700
tttaaatgac actgatttgt ttgtagttct tgctgcattc cgtagtggtg aaattgacat   35760
tttcactgtg aacagtttga acgacatgtt cattactcgt tgtgattcaa ttgcagacta   35820
cttcaaaaat tacgatggga tagaagttcc agaccatctt cgtccatata ttgattggga   35880
tgcagttgca aaagattatg gaagcgacta catcttctcc gaaggagtat tgttcttaaa   35940
tgtgtgattt aaatattgca aagctggagg ctggattgat tgtccaccac cagcctagaa   36000
acactttcta tcgtattctt gggcctacaa agattaaaac tcactgcgga agttgggtgg   36060
atgggtttgc ttaccaagaa gtgaagaaat acggggacca tactttctta agtatcgatt   36120
cctctactat ctacacacga ccgaaagagc tattcgactc agactggaaa acactatagt   36180
tccaggcggg tttcttcgaa gtgccaagcg ggttttgtgc tcgcattggc cttcggcttt   36240
agtctgaaac attagtggga tttgactttg ctgtatttac actagccatg tgagttacag   36300
gggtttgtga cagaatattt cttaataat gcttgacatt ctttttattt taagggcaaa   36360
aacactacac tattactcct atataatagt tcgttttga ttttaggaa atattgcttg    36420
acatgggcta aaatgcctga atgagggaaa tgtgaatatt atgaaagagc aaaacaatgc   36480
cagagtccgt gagtggctgt tggtgaatga gattctgtca gtgggtgatt tcccagactg   36540
gctggatgat gtgattacag gcgctgccag gctcaatggt agcgagttta acaccacaaa   36600
gcccaccagc cgtggtgtga ttttatctat gttactttgt cacgatgtgt tgtccacaga   36660
cacaatccgc gcaacattaa gcagaaagaa tgaagcaatt tatggtaagc ctgtgacagt   36720
tcgctacgca cagcttgtca aagcgcgtgt ttcatcggca tcaaaatcaa tcgaatactt   36780
ccttgaaaag agtaagaatt ctgattggtt ggcattgcaa gatgtttccg tgcaggagac   36840
acttgggcat tagttggaat tgaagaaaca acatcgtaaa ggattgctgc cacagtcctt   36900
tgagatggaa tgtttccatc atatacattt atcttttaac ataggccata gggccggaat   36960
acttcttcgc agaaaagcta ttcacttgtt ataggcgatg tattgggatg aattggaact   37020
aaataagcaa gctgctaggg ctgaataatt agagggttat gcctcatgct tatgttagtc   37080
attcgaaaat aggtttgtgc cacaagctgc tggtgctctg aggaagtcgg acaaacaggg   37140
cttagagtgg cataatccgc acaaaaccgc gccaccagct atgccaaagc gggtggattg   37200
ggtgaatgta ttgggaaggg ttgcaaagcc tctgtgacct ccgcagcttg ccagactgcg   37260
atgcagttat gatgcgtagg ccgcacccta acgggagtaa cccttcgcca atgcagttat   37320
ccagaattga cacaaacggt tggactatgg ccctaaaaca gggctatttt cgcaactctg   37380
tggcctgttt catgggccaa aagatgagaa gagaagtcac aaacactgaa tcgaaaattg   37440
gagagttcct atgattcgca agcattctgc taaagttttg acgttaagaa atgttctaag   37500
gtcttacaac gataaggtag aggaaacgtt gcacttcgtc cttattggtg ggaagtggtt   37560
gtataacggt acatcttccc taacacttct gagcagggct agttccgatg gattctggga   37620
atatgatatt aaatatatcc tggaaaatag tccggtattc agttacgaag aagtcatcaa   37680
gtatttctac gatggcccaa acaagtccat gcaaattgca acacgcgagt ggacgtcaaa   37740
tcgaccagtt tatgggaaac tatttaatg gctcgtaaaa cattgaagca aaagcttcgc    37800
aaacaaattc gtgaaatcaa atctgctgcc gaccaggaac atgaattggc tggcatcaca   37860
attaactttg aactccaggc aatgcaagct gttgctttag gtcatggcct tatgaccaca   37920
ctcattcatg ccaagaatgt gttgggagta aacagcgaag attaccaaac cattgagaaa   37980
gtggcgcaag agcgtatttc gcagtgcttg gtgaaattag ttgatatggg aattcctgct   38040
```

```
gaagaagcaa atcaccgaat cttacaaggt cactgatatg ttaacacaat ccagattaag    38100
ggaagttctc atatataacc tggagtctgg attgtttact tggaaggtat cactaagata    38160
tggtgatgct ggaaaggttg caggaactct ggataaagat ggctacataa ccataaggat    38220
tgatggccgt ctatacaggg cgaacagact tgcattccta tatgtccttg aagatttcc     38280 aaacggtgtt gcagaccata tagaccaagt ggttacaaac aatgcttgga ataatctaag    38340
ggaagcaacc tgcgtaacca acggctacaa taggaagaac agttcaaaca atacgtctgg    38400
agtaaagggc gtgtattggg acaaggttcg gaataagtgg gttgcaagaa tttcggtgaa    38460
caagcgaaga ttagttgttg gtgaattcaa caaactatct gatgcagagg ctgcaatagt    38520
atctgcgaga aacaagtatc acggagaatt tgctaatcat ggcctttgaa gatgataaag    38580
aaattgcatt acaaatctgt aagcaatggt taattgataa tgacgcatca tatctcgcca    38640
aagaagatgt tgttattatg tgggtgcatt tcaacccaga gtccaaaagg ggcgagtatc    38700
agagatacaa actcaaagag gcttgccgaa tcattaaggc aactcgtgcc ggacttgctg    38760
caatgaaata tattaggcca gagatgatta tgctggctgc tcaagaggaa gaacgtgctt    38820
ataaacaagc cgtgaaatct cgctccacag tacctcctga attctttaac ttagaacgtg    38880
cagggcattt taataattta gaaatgctaa cactgtgcct acttcaagaa ttagttggaa    38940
gaggaatgaa cattgaagct gttttgcctt gggaactcat gaaagagttg ttcttgacaa    39000
aaggctttgc tgtacctaat cgcacacttc gttggaaact gcttcgtgct gttgaaggtg    39060
aagctggtgt gattatccgt gaccgaacca accgcatgac cgtaacaggt gtgggacgtt    39120
ttgttgcgat tcaaatcgag ggcattgacg actcgattac aactgaactc actgtcgccg    39180
agacaaagga tttagtgatt aaatcaatcg aacgattcaa tatgtattga gttgtttgtt    39240
aaaacagagc agttctgaaa cattagttga atgtgaaaag agaaaggctc tttattcttt    39300
cataagtcgc gccaatggtg gcgtgcatta aatctacata aggtatatac aaatggctaa    39360
gattgtaacc gtaacccagt acgaagctaa cgatggttcc ctgttcctga gcgaagcaga    39420
atgtaacgca catgatttca aactggaaaa cggtgctaaa atcgacgcag ctgttgaagc    39480
gttcgctaac accatgaaac tggttgaccg ttctcgctcc atgcagagca acactgttgc    39540
atccttcctg gcattctacc tgccgtgggt tgaagctggt tgtccggaag ttgaacgtgt    39600
tgcgttcgat actccgaaag aagctaaagt tgctgacgca agtgttgccg aagctgccga    39660
agctgctgtt gaagaagctc cggtattcta agacagatgg agtcctctct tacgagaggg    39720
cttcaataac attacttacg agtggtgtta ttgaagtagt tttctgagtc ttacgacggg    39780
cctaaactgc ctgaagttat tgcgactgtt ttaaacacta aacacaagtg caaatgattc    39840
tgaaatgcga gttgcggctt aattaaattt aagtcctctc cgtggtcttc caatcccatg    39900
taaccaaatt tggcgcattg tggcttcgag atgtgattaa taaatcggag caataattaa    39960
tttgtattct gcgatgcaag gcaggcttaa gtccctcagt gcgcgtgggg atgtgacaga    40020
gtacaaactt aattatgcag ttggatattt ctagaggacg gacgagcaca ctggaatgtc    40080
ttcaattggt ttagtgtgag aagctatgcc aatatgaaac gtaactcctt gaggaagtgc    40140
tcctctagat ttccctccac acaggaacct caaacctgtg gcagcgactt cgaagctgca    40200
ctgtataacc taattcgccc taaagtgaat tgccctgagc acggaaataa actgctcaaa    40260
ccaatgatgc ccacaacggt gggataagtt aggttgcctg ttggtacttg ggttcaacac    40320
ctgcttgcac tcgcaaagta gtgcctcgta cctgagatga agtgagtcgg gaccatcaat    40380
```

```
cccacgttat gtcaaaacac agtaggcggc tcacagattc tacaagcctc gcagttcggg    40440
aaaacctgcg ttaccaaaac ccaccttacc aagcccagcc ccgttcgcag acaattgtta    40500
atatctgcat aacggctcta ggctattttt aataaccagc aacactggag tcctcatgga    40560
ttttgatgca cttgataatt tagacttcgg tgctgccgaa gaagcaattg aagaactgaa    40620
gaagaaacag gacgaagaag caatcgttcc tggtgctggc gataacgact gctcaagtgg    40680
tgcgtgcgcc atctaaggac gtatatgttt tcagagtgga taaatgaccc aggaagctct    40740
aaacaagcat acttgaagtt ttcactaaat ccagacaaaa cagttggtca tgtatataat    40800
ggtgattggg atttcaaagt tgtcgaattc aacccaccat atatgaaggt tatcgtactt    40860 caccccgcgca aagagtttga agtggagtat aattatgtta ggccagctta agtcaatctt    40920
tcttggcgtc ttgactgcat tgggtattct ccttgcagtg ttcctcaaag gcaaaagctc    40980
aggcaaagcc gaggagcgtc aggaagccaa agagaagcaa ttcgattcca ttaaagaatc    41040
tatcgagatt aaaacgcatg ttcagaaaga ggtgtctagc agttctgata gcaatgtcga    41100
tagtgagttg ctctcaaagt gggttcgtaa gtgattactg catgattgca caaccaatct    41160
atttggatgt tgcagaagtg aaagttctgt cacgcgaaac caaaacacag attttagtcc    41220
acaatgaaac gtgggcacaa aagtgttcga aacttacccg acagtgagtg aacaagacgg    41280
acgtctataa ctacccaaaa gtcgagggag tgcgcgactt taaataacga gactctagcc    41340
acttgtggca tggcaggtgt aattcctgca agttgttctg gcataacaa ttgaaattgc    41400 tgcctcgcat tgaacgcgag aaagttcagg tagtcacttc ctagaacagt ggccgggaac    41460
agacctagac aaaagtgctt gagaacgtta gctctgtctt gccagcatta atggcacgtt    41520
ggccgcgtaa aggccacagc gtctgaccaa cgtatcggtc aaccaaattc aatggattcg    41580
tagagttaat taaacctgca cgacgggata gggatgaagc atccgaggcc gactgtgtaa    41640
ttgctggctt actataaacc agccgaatcc gccaaatcaa tgggctagtg caaatgtcag    41700
tcactagaag atgtgttgca aaacgtcttc catgatgtgc aaagtgtcag tcacgtgccc    41760
accactttcc taacagttat gcctctgttc aaaaggctca agttagcgtc tggcataccg    41820
tagcgatacg gcttagttgc gctgattgtg ttgtgcagaa agaaagttca ggcttttatt    41880
tgggttactc ctcatcccga agttagctgg attcagaatc caggctatgt tcctatacac    41940
atgaaatatg caagtcgagg gttcttaatg ttcaaacatg atgcgagcat taagcgggtt    42000 tatactttc cccgatggtc cccataaaca aggctgattc acttgggcgg ttcgaatcaa    42060
atttaataag tgttttgtaa cagttcacgt caggacactt acttaaattt taactggaga    42120
gaaacatgaa aactgctgaa attgccgaag agatttataa ggccgtaata gccaaccaaa    42180
ttaccagtga agtcctgcac atggatattg aagaagttcg caatgccttt ggcggttttg    42240
caatcttgtc aatagaggct gcggaagcac tgacaagcac gtacaatcaa cgcgagtatg    42300
aaaagcgttc tgtactaaat gcgtcgctga agaaattca ggcgtcgtta aaataatacc    42360
attgttatgg tgcggagcta attaatctcc caccatatga accggagagc aaatgattac    42420
tgcaacactc gttgaccaca tgggcagcga cctcacaact gttaatgctg cacgagtttc    42480
ttatggtgca gagtcgcatg aaatgtctct gcgagatgag aagctgattg agtttcttgc    42540
aaagcataag cacattacgc cgttccgtca cgcacaggta acactgcgct gcaaagctcc    42600
aatcttcatt gcacgtcagc ttggcaaaca tcaaactggc tttagttgga atgaggttag    42660
ccgtcgttac aaagatggtg aagcaattga ggtcgaattc ttcattccag atactgtgtt    42720
tggtcgtcct gaaaagttga tgactcagac tgcgcagccg ttgccacaag attttgccga    42780
```

```
tgacattcaa tatcgtatgg aaagccataa caaggcttgc atcgtagaat atgaaatgtt   42840
aattggtttg gggattgctc cagagcaagc tcgcatggtt ctgccacaat ccatgatgac   42900
tgagtgggtt tggactggct ctctttatgg ctgggcatcc atgtacaatc aacgttcctc   42960
cgaacatgcg caatatgaag ttcgcttgtt tgcggaagaa gtgaataaaa ttatgtcaga   43020
actgtttccg atttgctgga aggctttgac caatcaggaa taatataaat gaacgtcaag   43080
caatgtgttg ccaagattaa gcacgatgta ccagactgta aatccacatc tggcaagtct   43140
ttacaggttt ggttgaatgt cgatgaagct ggtaataaga acttctctgg ttactgcttt   43200
gcatgtggcg ttctcgttcc gaatccgtat ggcaataatc cggagaatat tccggaaatt   43260
aaagtcaaga ctccagaaga aattcaggaa gaaattgacg aagtaacctc gtgccctcca   43320
tttgatttag accatcgcag tattgaacca gagttctgga aagctgctgg tgttcgccta   43380
ctctactcag agtttgatgg taagactcca aatgctttgg cgcatggata taccaagaat   43440
ggcaaacttg ttcgctggaa gattaaactt ctgaacaaga aagttatgtg gtcggttggt   43500
gacacccagg gtaacgaccc ttacaactgg atggctgcaa aagcaattgg cggtaagaca   43560
ctgttcatta cagaaggtga agaagactgt atcgcattgc gtcaaatctt gaaaactatg   43620
aaccgtggtg gtgcatatga agatttggat tttgctgtaa ttagtttgag tgacgggagt   43680
gattccgtac acaaatgttt gtcaccagtt gcagaagaaa ttaagcaacg ttgggagcag   43740
gttgttatcg tatttgacga cgatgaacct gggcgtaaag ctgcaaaaga agcgtgtcga   43800
ttgttgcctg gtgcaatgat tgcaactctt ccagctaatg atgccaacga ttgtctgaag   43860
cgtggcttgc tcaaagctac tcagtctgct gttgtattcc gtgctgctcg tcctcttcct   43920
acagcactcg tcaataaaga acttctcatg gaagagcttg atgacgaagt tgaacagggt   43980
gtggactatc cttggcccaa gttaacagac ttaatgtttg gtcaacgacg tgccgaagtt   44040
atctcaattg gtggtgcaga aggtggtggt aaaactacac tgtcacgaca gattgtgcat   44100
cacaacattg ttcagcatga ttggggagtg tttactgcat acatggagga aactcctaca   44160
gaaacactgc gccgaatggc tggccttaat gacaacttgc catattggga acctgcgttt   44220
actcgcgaag accctcgata tgatgaagct aagttccgtc aaactgctgc gaagatgctt   44280
cgtaacatgg agatttggga ccgcaagcaa gctggagaag acccttatga aacttgggat   44340
gggttaaaga caattcttcg tcagattggt ccagacattg atatgtttgt tcttgataac   44400
ttaacctact tatcggaagg gatttctgcc tcagagaaga acgacttctt aggcaagctg   44460
tatgcagaca ttactaagct agcagaccaa taccagttcc atgtcaatat cctgtcacac   44520
cttaaccccg tggcaaaagg tcagcgacct catgaagatg gtggacgtat caagaagtca   44580
gactttactg gctctcgtgc tgctgctaaa tattctcatg gcatgtttgg ctttgaacgt   44640
aatagtcagg cagttgaccc aaactgttct atcattcgtt ccattaaggc tcgtaagagt   44700
ggtaaaacag aaggctttaa gacttactac gacaccgaat ctggtcgaat cattcaacgt   44760
tcttgggaag attcactgtt cgaaactaaa gagattgttc aacttactaa gaagaacggt   44820
ccacatcaat aacagagctg ctgcgctgca tggttcgccc accagcgcag tcctccttaa   44880
tatggattaa gtaatgtccg atgaacaaaa gatttctctg tggcgaagta tgttttccta   44940
cacagaggat ggtaaacttt ataggaagat ggagtccggc aagttgaaac ttgttggtag   45000
cccttgtgga cgagataggc tctatttgaa tgtgcgtgtc gggaagtcct tcgaatacgt   45060
gcaccggatt atctttggga tgcactatgg attcttgcct aagcaagttg accacaaggt   45120
```

```
tggatttgac aactcccaa gcaaccttcg tgccgcaaac aaccaacaaa ataattgtaa      45180
cgtcgttagg aaacttggcg ctgtaccatt cagaggtgtg tccaggttga agaatggaac    45240
gtatacagca aaaataagaa atggaaactc aagaatatat attgggacgt tcgcactgc     45300
cagacaagct gcaatggcgt acaatgaatt tgcaataaaa ctccacggag agtttgcgat    45360
aatcaatagg aacatatgat gctctatcct tggaaagata tgtatgccag tgacattgaa    45420
acaactggtt tgttggagca gatgaggaaa caggctgcac cacgtcttca caacattgga    45480
tacattgatg ttcaaactcg tgaagaaact gtgattgagt ggacgcaacg aaaatccatt    45540
caagactttc tggacacagg tccaacacta atcatgcaca acggcgcaac ctttgacttt    45600
gaagcattga agttccttgg ttatgacgtt tcaaaatgta ctctgattga tacactattt    45660
atcagtggt atctccaacc tcgtcgtgtt aagcatggac ttgaaggtta tggtgaagag     45720
tttggtgtgc ctaaaccagt cattgacgat tgggaaaatc aaactcagga agaatataac    45780
catcgtgtga tggaagactg taagattcag ttaaagctgt gggaacagca atatattcaa    45840
ctcctcaaaa tttataaatc tcctagcgaa gttaaacgct tcattgaata cttgatgacg    45900
aaagctcgcc aacaggttat tcagcaacgt actcgttgga agttgaacat tgagaaggca    45960
ttggcatta aggccaagct ggaaccaatg attaaagaga gaccgacgc attggaagca      46020
tcaatgccgc gtattcctga agttgtaatt aagactcgtc cagccaaatg ccacaagatg    46080
aatggacagt tgtctgctgc tggcttgaag tggaaagcta tttgcgatgc gaatggcctg    46140
gactggaaag acccagagat aggcatcaaa attatcaagg gctacaaaga accgaacgct    46200
ggttctcacg tacagattaa ggattggttg ttcagcttag gctgggtgcc agaaacattt    46260
aagtttgacc gcaataagga aacaggtgaa actcgccaga ttcctcaaat cactgtgaag    46320
gatgaagatg gcaatcctga aatatgtcca agcctccata agttggcaga agaaaccc      46380
gaatctggca ttcaacatct tattgggatg ggcgtgtata acaccgtct gtctgttgtt     46440
aacggttttc ttcgcgacgt cgatgaagac ggatacctta ctgcacgatg tggtggcctt    46500
accaatactt tacgccttaa acatcgcgaa cttgttaacc tcccttctat tcgtgtattt    46560
ggcggtgaag aactgcgttc aatgctggaa gcgtggcgtg aagactacga acagttaggt    46620
tctgacttgt gttccttgga agaccgttgt aaacaccact tccaatggat gtatgaccct    46680
gaatatgtta agaagcagtt ggcaccagac tatgatgctc accttgcaat cggcgtaatc    46740
ggtggattta ttaccgaaca agaatctcag gaccacaagg acggaattaa gaagtgtaaa    46800
caacgtccaa tgtttaagac cacgaactat gcgtaaattg atgcgcatgt aaaatccctt    46860
taattcggtg gaactctctg ccgcagagac aataccgagc gaagcatgaa aagaaattac    46920
caacctgctt tcatgaacgt gtaacgacta gccgtaaggc gtacacccaa gtgggtggaa    46980
acggggggacc cgacataggt cggtgatgat atagtctgct ctgcatggtg acatgcagct    47040
ggattcgttc cggcatgaaa ttaacgactt cgtgtgaaca atgtaaatgg tcaatatggt    47100
gctggtattc ctactgtagc tcgttctgct agctgtgacc agactactgc tgcacgactg    47160
cataaagcat attgggactt gaactggtct attaaagaga ttgctgctaa cactaaagtt    47220
atcacagttg atggtcagat gtggcagcag aatccagtaa acaaattctg gtattcattg    47280
cgtacagaga agaccgcctt ctccacattg tgtcagggca ctggtgcata tgtgtttgat    47340
atttggtgta acaacattat tgcaatttgc aacgaacgtt ggggctgcga ccgcttctg    47400
tctggacaat tccacgatga attgattctc caggttaaga aaggcttccg tgatttgtgg    47460
acggacttgc ttaatgaagc aatggaccga accaacaaag aacttaaact caatcgtgat    47520
```

```
tgtgcatgtg atgtacaatt tggcgataac tacgcagaga ttcactaatg gttgttgtat    47580
ctatattcga caaagtggac catttccatt ttgtcaagaa aggcgaagac gcacgggaag    47640
ctgtgctgtc tgtaattacc gagaatgctg aaacattatt tggaagtgat tatgatacca    47700
atccaatgta tcaggcattc gttaaaactt tatctagtcc tgccgtcaat gagcaagagt    47760
taatctcttg tatgaacgac ctggacttct ccctagttat cactcaactg taatttaaag    47820
gtactcaaaa tggcatttgc tgctcctacc ctggcctcga acaagactcc ttctgctgca    47880
ccattactgg aagcgggtgg ttatcctgct cgtgtttgcc gtattatcga cctgggctta    47940
cagcctggtt ctgctaaata tcctaccccg tctctgaaac ttctggttac tttcgaattg    48000
ctcgacgagt acatgaaaga agttgacagt gaaggtaaaa tggtcatggt tcaagaccca    48060
gacgaagatg acggcatcat gatggcgaag aatcttgaag acaagccgcg ttggtttgac    48120
tttgagttta cctataatgc tgacggcttc atgggcgaga actcccacat ctacaaattc    48180
gctaaagcga ttgatgcact ggaagttaaa cctaacctgg aacaaggtat tcagggccat    48240
cctgccaaga acctgccaga ttggttgggc gaacctctga ttgttggcat tgttcagtat    48300
accaagcagt ccgtaagaa tgctggccag gttgcaaaca aagttgctac cttctctccg    48360
atgaaatcca aagagaagaa agaagctaaa gcactggtta acccgactgt cttcttcgac    48420
atgtccgagc cggacctgga agtattcaac aagctgcctg gtggcgaatc tccgtatgca    48480
atcaagaacc gcattacttc cggtgttgat ttctacaaga ctaagctgtc tgctctgtta    48540
ggtggcaaac ctgccgatga tggtgctgta ccgaatcagg cttctgatga agaagttgat    48600
gcagccatga aagctgaact ggaagcacaa gctgctgcga agcacagcg tgaagctgaa    48660 ggtggtgcaa gcacgactgc catgccgttc taactataaa tatggctcct tcgggagcct    48720
ttaattttgg agcttaccaa agtgagtaag aaacgagtat tgttgctggt cgattttgat    48780
atggtggcat ttagccattg tgcggcagaa gaatttggga aagagccaga agatataaat    48840
ttctcgaaga ttcaaatgtc aatggactct aagatggagt tcttgtctaa gcgttctggc    48900
gcaactcatg tcatgggttt cgtatctcct tctaagacaa tgcgaaacgt gtttgccgaa    48960
aattataaag gcaaccgcga taacgtatgg cgtccagaga acttaaagaa tgccaaggcc    49020
cacttgcttg ttgcatggaa tgggtattgg atgaaaggtc tggaagcaga tgacctcctt    49080
gctgtattcg cacgtcatga atatgacatg acaatgggta acgtaatga gattaagagc    49140 ctcactcgta ttggtccgtg cacatatgat gaagtctgga ttgcatcgtt ggacaaagac    49200
ttgcgccaaa tcgggcagaa cggtggtgtt ggtccggtaa tcaaacacta ccaatgggaa    49260
cgtgaaaccc agggcattgg tgagaaaatt ataatcccta agattatgg tgaactcaaa    49320 ctaatcatca aggacaatgg caaaacgaag aagaaagaag ttaaaggcaa tggccctaaa    49380
ttcttcttgc atcaattgct tattggcgac tcaacagata acgttatggg ttgcggagtt    49440
cttgaagaaa agatttacaa aactggtgcc aaagccggag aaacttattt ccgtcgtgat    49500
ggcgttggtg cagttgcttc attcgagatg ctggatggta caacctccta tgcagaaggt    49560
ttgaagaaag ttattggtgc atatattatg cgcttcggag atggttggga acaggagctg    49620
ctcaaagtgg cccgccttgt ctatatgcac catcaaattg aaaagggtaa ttgtgttcgc    49680
ttgtggcatt acaagaacat taacgaatac tttgacctta agagaatcg tatcctcact    49740 caagaagagt acctccagaa ataattggag ttggaatggc ttacggttat tgtgaacgg    49800 aagccaagtt tgtatcttgg ctccaatctg ctattcgaag tgtttggtct aaacacccaa    49860
```

```
gcaaacttgc gctaatacaa tctcgacgca ttgcattgaa ggtcggtggc tcaaagaaac    49920
caatcttcca cattcaatgc taccattgca agaagttgta taagctcaaa gagattgaag    49980
taaaccacaa agttcaagtt ggtggcctcc ttaagttgga ggatttacac cgctttgtgg    50040
acaacctact attggttcag ccagaagatt tggaattgct gtgtaaagat tgtcacagca    50100
ttattacata catggaacga tatggtgtgt cacgtcgtga tgcagtcatt gagaagaagt    50160
gtattgcatt tgccaaacta actgacgaag agcaaattgc caagtgcaat cttgccaaaa    50220
tagagccagt tcctaaaacc aaaatcggac gcaagaacgc tgttcgagaa tacctgagaa    50280
agaatcttaa tgtctattaa gctcctcgct gatggtacaa gatatacaaa ggctcacgca    50340
catgattggg aagacccaaa ctgtcttatt cgtggtcgat gcgaattgta catcaaaatt    50400
gacggcatac gagcgattcg taatgcttct ggtgaggtat ggagccgcaa ctctaaacct    50460
ctccctcact gcgaccatct caaatttaaa gatgcagaaa tctttcgcgg ttcctggaac    50520
gagacttcat ctatccttgg gcgtatcgac cctccgacca taccgttatc gcaagaaaac    50580
gtttatgagt tgagtgatgg tgctgttgac ccacgcctgt acatcggctg gtgcaaggac    50640
ccaagcaatg aaaaccttaa ggcattgatg gataaatatc tggcgcttgg tcatgaaggt    50700
attattgtcc gtgatgcaaa aggtaaatgg tggaaggtcg ttccgtattt gtatgccgac    50760
gttcgtgtaa caggtatgaa agaaggcact ggtgcactca aggtatgtg cggctccatc    50820 tctacagcat acggctctgc tggctctatg gtgaaagatt gtctttcctc tgtcggtgtt    50880
ccagaagata acatagcaat acgccgttgg ttgtggagcc acaaggatac actaattggc    50940
tcgattattc aagtccggta tcgtgaaaag acagaggctg ggaagtttag attcccatca    51000
ctggtgagac tgcgtaccga caaaaatgaa gagagcctcg attgattacc caagaaagat    51060
taaaacaact ttaccactac aacgagttgt caggtctgtt cacacacttg gttacaggaa    51120
aggttgcagg atgttacaac aaggtatacg ccactatagg catagactat gggacgtatt    51180
cagtgcacca actggccttc ctgtacatga cgggaaaaat tccaaagtgc atagaccata    51240
tagacagaga taaacataac aatgcttggc acaatctccg tgaagctact ttctcagaga    51300
acctgcataa tgtaggaacc acaagtagga actcaaccgg agttaaggga gtttcttttg    51360
attctaagag acgcaagtat tgtgcacaaa tctgtgtaaa tggttccaga aaatttcttg    51420
gcagattcag ttccttacaa gatgctgaaa atgccctact ggagtataga catgactaat    51480
ctcgctgtaa ttctaaatgg cccacctggt tgcgggaaag acactatagc caacttaatt    51540
gtagaacggt gcaactccct caatccagtc atcaaacatc aatttaagga tgcactgtat    51600
gagcacactg ctaaacatta tcaagttgac ttggataagt ttatccattt cgccagtgac    51660
cgcgagctta aagactccgt gtcgttggct gggctgcacg ggaaaacccc gcgtcaggca    51720
ctcattcatg ttagcgaaga catatgtaag cctcgctacg gtaatggtta ctttggctcg    51780
gttgaagcta atcgtatccg cgaacttaag gggcgtgtac gtggccctat taatgtcatt    51840
tatcccgatg gtggcttcgg agatgaagtt ctcgcaattg agtctgagtt tgattgtgta    51900
cttattgtgc gccttcatcg cgatggctat gatttcgcgg gcgattctcg taattacctc    51960
aacctgccaa acactaaaac acgttggtca gttgacgaac accttttaaa taataaaatc    52020
tttgatggtg tctggaaagt tgaaaactgg atggaccgaa tcaaatggag catcgaaaaa    52080
tgagttgcat cacccaagtt gttgctgtaa agcgagtgca tcctaatgcg aaattacctg    52140
tgtacgctac tgctggcgct gctgctgctg acgtttgcac tatctccgat agcactgttg    52200
ttatcaatcc cggctgctct gctgttttcg atactggcct ccagttcgaa gtaccagttg    52260
```

```
gatacgaact caaagtacat agccgttctg gtcacggctt taagtctggt attcgcctgg   52320
caaactgcac aggaattctg gactccgatt atcgtggcaa tcttatggtt aagctgcaca   52380
atgactcgga cacagccttt gtggttcagc caggtgaacg tatttgtcag gtgcaagtta   52440
gtaaagctac tcaacaccat ttcgttgaag ctgtagaact taataccaca gagcgtggaa   52500
cttcgggttt cggttctaca ggcagagttt agtagattgt ggagaaacca ctctaactta   52560
ttggaaccta attgaaatga aactgtcctc tcctgttgta gtaaataatc gcaaagttaa   52620
atttgcatac ctcaagtcta atgtcacctc tactggtggc gggacttatc tcacccgtgc   52680
acttgcagtt cgcaacgaaa caggtgcgga tgttatcgtt ttcatgcttc ctcgtggtga   52740
gaacacaatc aagaacgtcg aacgtatcaa gcgtgggcgc gaagatttaa tgtcggctgt   52800
taagccgctg atactgccat ttaagattgt ggtggttgtt ggttctaccc aagcatatct   52860
ggaagatttc tataaagata tggcctggag cgatattaaa tattaagcga cacgcgtaat   52920
tagggaggct atctggcctc ctatcttatt cggagtcgct tatgcgcaca atacaatgtc   52980
ccaactgcca ttatgaaatt gcagaagatg atttcataac gcagcaatgt cctatctgtg   53040
attcatacat gccactaaac cgcctgtatt taaaggccga ttctggttta ggcagcatca   53100
ttcgcatcaa tcccgtgcaa actcagccat tagtggattg tgattaaaaa caaagagaac   53160
gaatcaatgt caaaaactga agatttgggc ccagagttta acgatgcagt tgccagctat   53220
ctcgttaaga actacgggga cgtactcaaa gtttccagag aaagattctg tattctgtct   53280
ttgccattgc tccgtcgata tatttcagaa aatactgcaa tagttgacag ctatgaagaa   53340
caaattcaag cagagttaga aggccagggt cttgaaaacg atgctgtact gcgttcagtt   53400
ttcagagcac aacttgagcg tcttcgctct ggcgacaaga aagactcgac tgcctatgca   53460
gatgagttga agaaaggtat tcaagcaggt gttactgacc gtgttgcagg ttccactttg   53520
gaggagccta actcggagta cgataacacc gatgaacttg tagacaagat tctgcatgac   53580
ccacataacg tggacccaac tgtaatccct gccaaggttg cagaacgtgt tcgcaaaatc   53640
ttgatgaaaa gtttcgaagc ctttggtaaa tggcagttcc atatccaaat gggatttcca   53700
tttcaagcac aagactttca cgatgtaata ttcagtgttg gccagaaggt tgttgatggt   53760
gagattgacc gcttaatagt gaccattcct ccacgacact ctaagactca gctcatgagt   53820
attgcattgc ccttgtattc attttgccac aatgaatcaa gccataacat tatcacctcg   53880
tatgcagaag acgttgttct tgaatcgagt ggttacatcc gtgctgtaat gatggaccca   53940
ctattccaac gcatattccc gaaggtgaga atagacccga acaaacgttc tcttgagcgt   54000
tggggtacga ccaaagctgg tgtaatgcac gctgttccta ctggtggtaa gctaactggt   54060
aaaggtgctg gactactggt tgcaaactat tccggctgct ttgtggtcga tgacgtaatc   54120
aagcctaaag atgcctactc cgacacagtt cgagcagaaa tcaacgaccg gtcttgcgaa   54180
tgatggttgc ataaccgact                                               54200
```